US008217797B2

(12) United States Patent
Ikoyan

(10) Patent No.: US 8,217,797 B2
(45) Date of Patent: Jul. 10, 2012

(54) POSTURE TRAINING DEVICE

(76) Inventor: Dikran Ikoyan, Glendale, CA (US)

( * ) Notice: Subject to any disclaimer, the term of this patent is extended or adjusted under 35 U.S.C. 154(b) by 400 days.

(21) Appl. No.: 12/560,173

(22) Filed: Sep. 15, 2009

(65) Prior Publication Data

US 2011/0063114 A1  Mar. 17, 2011

(51) Int. Cl.
*G08B 23/00* (2006.01)
(52) U.S. Cl. .................................................. 340/573.7
(58) Field of Classification Search ............... 340/573.7, 340/669, 671, 539.1, 566, 572.1; 702/141; 600/595
See application file for complete search history.

(56) References Cited

U.S. PATENT DOCUMENTS

| | | | |
|---|---|---|---|
| 4,730,625 A | 3/1988 | Fraser et al. | |
| 4,872,841 A | 10/1989 | Hamilton et al. | |
| 5,143,088 A * | 9/1992 | Marras et al. | 600/594 |
| 5,398,697 A * | 3/1995 | Spielman | 600/594 |
| 5,749,838 A * | 5/1998 | Kline | 601/71 |
| 5,868,691 A | 2/1999 | Vishnevsky | |
| 6,540,707 B1 | 4/2003 | Stark et al. | |
| 6,554,781 B1 | 4/2003 | Carter et al. | |
| 6,827,694 B2 | 12/2004 | Gladoun | |
| 7,317,849 B1 | 1/2008 | Meneghini et al. | |
| 7,431,703 B2 * | 10/2008 | Salvi et al. | 600/594 |
| 7,602,301 B1 * | 10/2009 | Stirling et al. | 340/573.1 |
| 7,634,379 B2 * | 12/2009 | Noble | 702/141 |
| 2008/0204225 A1 | 8/2008 | Kitchen | |
| 2008/0214963 A1 | 9/2008 | Guillemaud et al. | |
| 2008/0319352 A1 * | 12/2008 | Chow et al. | 600/595 |
| 2009/0043230 A1 | 2/2009 | Davis-Havill | |
| 2009/0054814 A1 | 2/2009 | Schnapp | |
| 2009/0062092 A1 | 3/2009 | Mortimer | |
| 2009/0093678 A1 | 4/2009 | Kimura | |

OTHER PUBLICATIONS

Analog Devices, Inc., iMEMS Accelerometer, 2007, Norwood, MA.

* cited by examiner

*Primary Examiner* — Phung Nguyen
(74) *Attorney, Agent, or Firm* — Milord A. Keshishian

(57) ABSTRACT

Sensory indication modules intimately associated with a surface for detection of angle relative to true vertical and acceleration, and include feedback indicators for communicating localized information in relation to the detected angle and acceleration. Further included is a control module for communicating command and control instructions with the sensory indication modules.

9 Claims, 18 Drawing Sheets

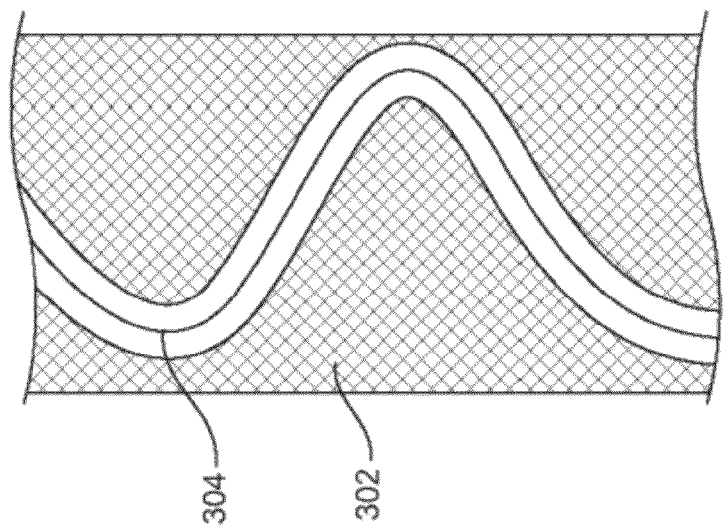
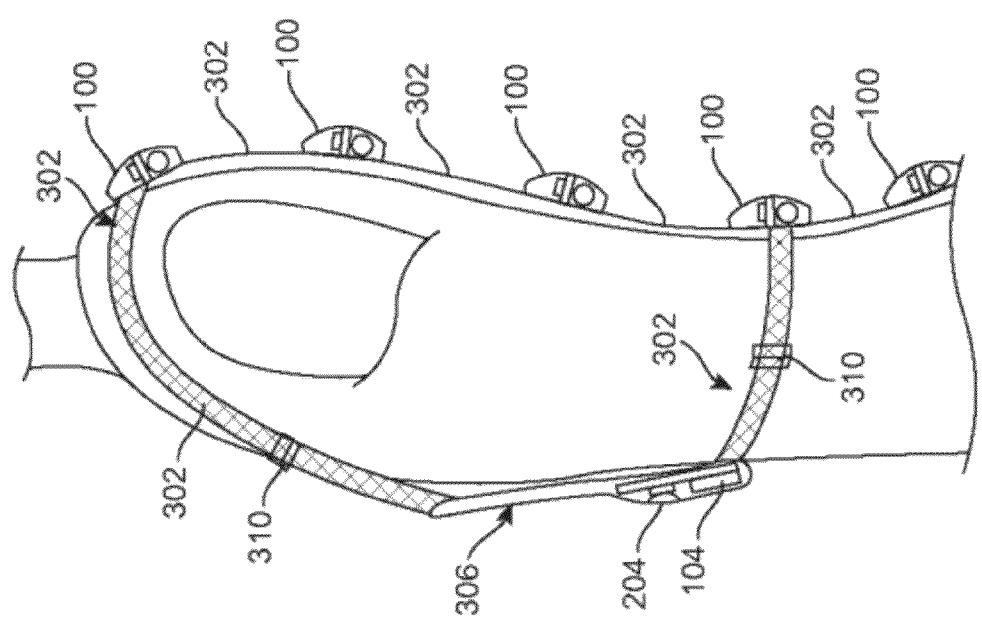

POSTURE TRAINING DEVICE

BACKGROUND OF THE INVENTION

1. Field of the Invention

This invention relates to monitoring apparatuses and methods for using and constructing the same. And, more particularly, to monitoring apparatuses and methods for posture training to condition and encourage desired posture practice for a given activity.

2. Description of Related Art

Conventional back posture training devices have been known and used for many years. Most conventional back posture training devices suffer from various disadvantages in that they attempt to correct back posture by attempting to correct only the relationship (e.g., orientation) of the various segments of the spine relative to one another, while ignoring the orientation of the whole spine in relation to the rest of the body and in relation to true earth vertical. In other words, the segments of the spine may have correct relationships with respect to one another, but the entire spine may be at an incorrect angle leaning forward, backward, or be at one side while the individual segments within the whole of spine continue to maintain their correct respective relationships. Most conventional back posture training devices would not infer as bad posture if the segments of the spine maintain the correct relationships while the whole of the spine is leaning forward, backward, or is at one side. This could result in chronic sharp back pain.

Accordingly, in light of the current state of the art and the drawbacks to current conventional back posture training devices, a need exists for a posture training device that would correct posture in relation to a reference for a given activity.

BRIEF SUMMARY OF THE INVENTION

One exemplary optional aspect of the present invention provides an apparatus, comprising: sensory indication modules intimately associated with a surface for detection of angle relative to true vertical and acceleration, and includes feedback indicators for communicating information in relation to the detected angle and movement. Further included is a control module for communicating command and control instructions with the sensory indication modules.

An exemplary optional aspect of the present invention provides an apparatus, wherein: the sensory indication modules are encapsulated within a soft casing.

Another exemplary optional aspect of the present invention provides an apparatus, wherein: the control module includes a controller encapsulation layer.

Yet another exemplary optional aspect of the present invention provides an apparatus, wherein: the sensory indication modules and the control module include a set of fastener mechanisms for detachable coupling the sensory indication modules and the control module with a module support.

Still another exemplary optional aspect of the present invention provides an apparatus, wherein: the set of fastener mechanisms provide power and communications signals between sensory indication modules, the control module, and other devices.

A further exemplary optional aspect of the present invention provides an apparatus, wherein: the surface is a vertebra, and the sensory indication modules are intimately associated with the vertebra by a module support.

Still a further exemplary optional aspect of the present invention provides an apparatus, wherein: the module support is comprised of one of a garment and a strap.

Yet a further exemplary optional aspect of the present invention provides an apparatus, wherein: the module support is comprised of one of a garment and a strap with embedded wiring.

Another exemplary optional aspect of the present invention provides an apparatus, wherein: the module support further includes a cover that covers the sensory indication modules and interconnections, preventing the sensory indication modules and the interconnections from snagging with other elements. The cover includes a set of cover fasteners that coupled the cover with the module support.

A further exemplary optional aspect of the present invention provides an apparatus, wherein: the strap includes sensory indication module adjustment fasteners to enable adjustment of the position of the sensory indication modules along the strap.

Yet another exemplary optional aspect of the present invention provides an apparatus, wherein: the control module and at least one sensory indication module are integrated as a single unit.

A further exemplary optional aspect of the present invention provides an apparatus, wherein: the feedback indicator is a vibration mechanism.

Another exemplary optional aspect of the present invention provides an apparatus, wherein: the sensors are miniaturized multi-axis accelerometers.

Still a further exemplary optional aspect of the present invention provides an apparatus, wherein: the control module includes a Printed Circuit Board assembly, including:
 a microprocessor;
 communication unit that enables the control module to communicate with sensory indication modules and external devices;
 a power source; and
 an interactive unit for activating the control module, setting references and manipulation of the control module.

Another exemplary optional aspect of the present invention provides an apparatus, wherein: the control module and the sensory indication modules include a communication unit that enables communication between the modules and external devices.

A further exemplary optional aspect of the present invention provides an apparatus, wherein: sensory indication modules intimately associated with a vertebra for detection of orientation and acceleration of the vertebra, the sensory indication modules include:
 an identification (ID) mechanism for identifying a sensory indication module that generates a unique analog ID signal;
 a sensor for sensing the angle of the vertebra in relation to true earth vertical and acceleration, and generating a first analog signal;
 an Analog to Digital Converter (ADC) for digitizing the analog ID signal and the first analog signal for processing by a microprocessor;
 a sensor activation mechanism for periodically activating the sensor for detection;
 a memory unit for storing data for use by the microprocessor and for storing detected angles and references;
 a timer for synchronization of various functionalities of the sensory indication modules;
 sensory indication module communication unit for communication of signals with the microprocessor and external devices;
 a feedback indicators for communicating improper angular orientation of the vertebra with which the identified sensory indication module is associated.

Still another exemplary optional aspect of the present invention provides an apparatus, wherein: the ID mechanism is an impedance that generates the unique analog ID signal that identifies the sensory indication module for unique association of the identified sensory indication module with a specific vertebra.

Yet another exemplary optional aspect of the present invention provides an apparatus, wherein: the sensor is a miniaturized multi-axis accelerometer.

A further exemplary optional aspect of the present invention provides an apparatus, wherein: the sensory indication module communication unit is asynchronous receiver transmitter.

Another exemplary optional aspect of the present invention provides an apparatus, wherein: the feedback indicator is a vibration motor that is actuated by a vibration actuator based on a command from the microprocessor.

A further exemplary optional aspect of the present invention provides an apparatus, comprising: a control module for communicating command and control instructions, the control module includes:
an interactive unit for activating the control module and for setting references;
a microcontroller with an associated program memory having fixed set of instructions, a non-volatile memory, and a Random Access Memory (RAM);
a timer;
communication unit that enables the control module to communicate with the microcontroller and external devices;
power source provides power to the control module and external devices.

Another exemplary optional aspect of the present invention provides an apparatus, wherein: the external device is a sensor and a feedback indicator.

Yet Another exemplary optional aspect of the present invention provides an apparatus, wherein: the microcontroller activates all sensors together via an electronic switch.

A further exemplary optional aspect of the present invention provides an apparatus, comprising: sensory indication modules intimately associated with a surface for detection of angle and acceleration, and includes indicators for communicating information in relation to the detected angle and acceleration;
control module for communicating command and control instructions with the sensory indication modules;
a power bus and a single wire serial bus that couple the control module with sensory indication modules.

Another exemplary optional aspect of the present invention provides an apparatus, comprising: sensory indication modules intimately associated with the vertebra for detection of angle and acceleration of the vertebra, the sensory indication modules include:
a sensor for sensing the orientation of the vertebra in terms angle and acceleration in relation to true earth vertical, and generating a first analog signal;
a feedback indicator for communicating improper angular orientation of the vertebra with which the identified sensory indication module is associated;
a control module for communicating command and control instructions with the sensory indication modules, the control module includes:
an interactive unit for activating the control module and for setting references.
a microcontroller with an associated program memory having fixed set of instructions, a non-volatile memory, and a Random Access Memory (RAM);
a timer;
communication unit that enables the control module to communicate with external devices; and
power source that provides power to the control module, the sensory indication modules, and external devices.

Still another exemplary optional aspect of the present invention provides an apparatus, comprising: sensory indication modules that include a microprocessor;
the microprocessor periodically determines if there is a wake up command from a microcontroller of a control module;
if the microprocessor determines that there is no wake up command from the microcontroller of the control module, the microprocessor reverts back to sleep mode;
if the microprocessor determines that there is a wake up command from the microcontroller of the control module, the microprocessor is activated, which, in turn, activates a sensor for a first duration, and clears receiver buffer;
the microprocessor determines if there is a new command received from the microcontroller;
if the microprocessor determines that no new command is received from the microcontroller, the microprocessor reads angles of a vertebra through a sensor, saves the read angles, and determines if the first duration has expired;
if the microprocessor determines that the first duration has expired, the apparatus is entered into a low power sleep mode by the microcontroller of the control module;
if the microprocessor determines that the first duration has not expired, the receiver buffer is cleared, and the microprocessor determines if a new command is received from the microcontroller;
if the microprocessor determines that a new command is received from the microcontroller, the microprocessor checks the received command ID to determine if the received command from the microcontroller is intended for the sensor to which the received command is sent;
if the microprocessor determines that the command received from the microcontroller is intended for the sensor to which the command is sent, the microprocessor determines if the command received is an angle query command; otherwise, the receiver buffer is cleared;
if the microprocessor determines that command received is an angle query command, the microprocessor sends the saved sensed angular orientations to the microcontroller, and the receiver buffer is cleared;
if the microprocessor determines that command received is not the angle query command, the microprocessor determines if the command received is a command to activate an indicator;
if the microprocessor determines that command received is a command to activate the indicator, a second duration is set for activation of the indicator, the indicator is activated for the second duration, and the microcontroller enters the apparatus into a low power sleep mode;
if the microprocessor determines that command received is not a command to activate the indicator, the microprocessor determines if the command received is a reset command;
if the microprocessor determines that command received is a reset command, the microprocessor clears and resets all registers, and the microcontroller enters the apparatus into a low power sleep mode.

A further exemplary optional aspect of the present invention provides an apparatus, comprising: a control module that includes a microcontroller, which is generally in a power save mode for a first adaptive time period, with a duration of the first adaptive time period varying depending on responses from external devices;

the microcontroller periodically determines if the first adaptive time period has expired;

if the microcontroller determines that the first adaptive time period has not expired, the microcontroller determines if an interactive unit has been actuated for one of a first and second actuation durations, with the first actuation duration shorter than the second actuation duration;

if microcontroller determines that the interactive unit has not been actuated for one of the first and second actuation durations, the microcontroller maintain the power save mode;

if the microcontroller determines that the interactive unit has been actuated for second actuation duration while the first adaptive time period has not expired, the microcontroller deactivates the first adaptive time period, and places the apparatus to OFF mode;

when the apparatus is OFF, if microcontroller determines that the interactive unit has not been actuated for one of the first and second actuation durations, the microcontroller and the entire apparatus remain OFF;

further, when the apparatus is OFF, if the interactive unit has been actuated for second actuation duration, the microcontroller is activated, recalls saved users preferences, and activates the first adaptive time period; if the interactive unit has been actuated for first actuation duration, the microcontroller only activates the first adaptive time period, and enters the power save mode;

if the microcontroller determines that one of the first adaptive time period has expired and the interactive unit has been actuated for the first actuation durations, the microcontroller forwards a first command to external devices;

the microcontroller further forwards a first query to the external devices, and receives a first response to the first query;

the microcontroller determines if the first response has been received from all external devices; if the microcontroller determines that the first response has been received from all external devices, the microcontroller determines if the interactive unit has been actuated for the first actuation durations;

if microcontroller determines that the interactive unit has not been actuated for the first actuation durations; the microcontroller determines if a user preferred reference is set;

if microcontroller determines that user preferred reference is not set; an indicator is activated and the first adaptive time period is modified for a longer duration, increasing the duration of the power save mode of the microcontroller;

if microcontroller determines that user preferred reference is set, the microcontroller compares received responses with user preferred references; if received responses are commensurate with user preferred references, the first adaptive time period is modified for a longer duration, increasing the duration of the power save mode of the microcontroller, otherwise, an indicator is activated and the first adaptive time period is modified for a shorter duration;

if microcontroller determines that the interactive unit has been actuated for the first actuation durations; the microcontroller sets received responses from external devices as user preferred reference.

Another exemplary optional aspect of the present invention provides an apparatus, wherein: set user preferences are communicated externally for display and analysis.

Yet Another exemplary optional aspect of the present invention provides an apparatus, wherein: comparing the received responses with user preferred references includes:

obtaining a plurality of responses Data($Ta$), Data($Tb$), ... Data($Tm$) at different time intervals $Ta$, $Tb$, ... $Tm$, with m an integer interval;

calculating an average AVG of the plurality of responses obtained at different time intervals:

$$AVG(Channel)=(Data(Ta)+Data(Ta)+\ldots+Data(Tm))/m;$$

calculating simple deviations from the average of the plurality of responses obtained at different time intervals;

$$\Delta(Ta)=ABS(AVG(Channel)-Data(Ta))$$

$$\Delta(Tb)=ABS(AVG(Channel)-Data(Tb))$$

$$\Delta(Tm)=ABS(AVG(Channel)-Data(Tm))$$

determining the maximum deviation MAX DEV;

$$MAX\ DEV(Channel)=MAX(\Delta(Ta),\Delta(Tb),\ldots \Delta(Tm));$$

repeat for every channel;

the microcontroller determines if the AVG(Channel) or the MAX DEV (Channel) are outside defined maximum parameters, and if so, set the first adaptive time period duration and disable the feedback indicators;

otherwise, microcontroller determines if AVG(Channel) is outside the user set preferences; if the microcontroller determines that AVG(Channel) is outside the user set preferences, microcontroller determines which specific parameter within AVG(Channel) is outside user set preference, and generates a unique indicator specifically associated with that parameter, and sets the first adaptive time period duration to a shorter duration;

otherwise, set the first adaptive time period duration to an average duration.

Such stated advantages of the invention are only examples and should not be construed as limiting the present invention. These and other features, aspects, and advantages of the invention will be apparent to those skilled in the art from the following detailed description of preferred non-limiting exemplary embodiments, taken together with the drawings and the claims that follow.

BRIEF DESCRIPTION OF THE DRAWINGS

It is to be understood that the drawings are to be used for the purposes of exemplary illustration only and not as a definition of the limits of the invention. Throughout the disclosure, the word "exemplary" is used exclusively to mean "serving as an example, instance, or illustration." Any embodiment described as "exemplary" is not necessarily to be construed as preferred or advantageous over other embodiments.

Referring to the drawings in which like reference character(s) present corresponding part(s) throughout.

DETAILED DESCRIPTION OF THE INVENTION

Figure 1:
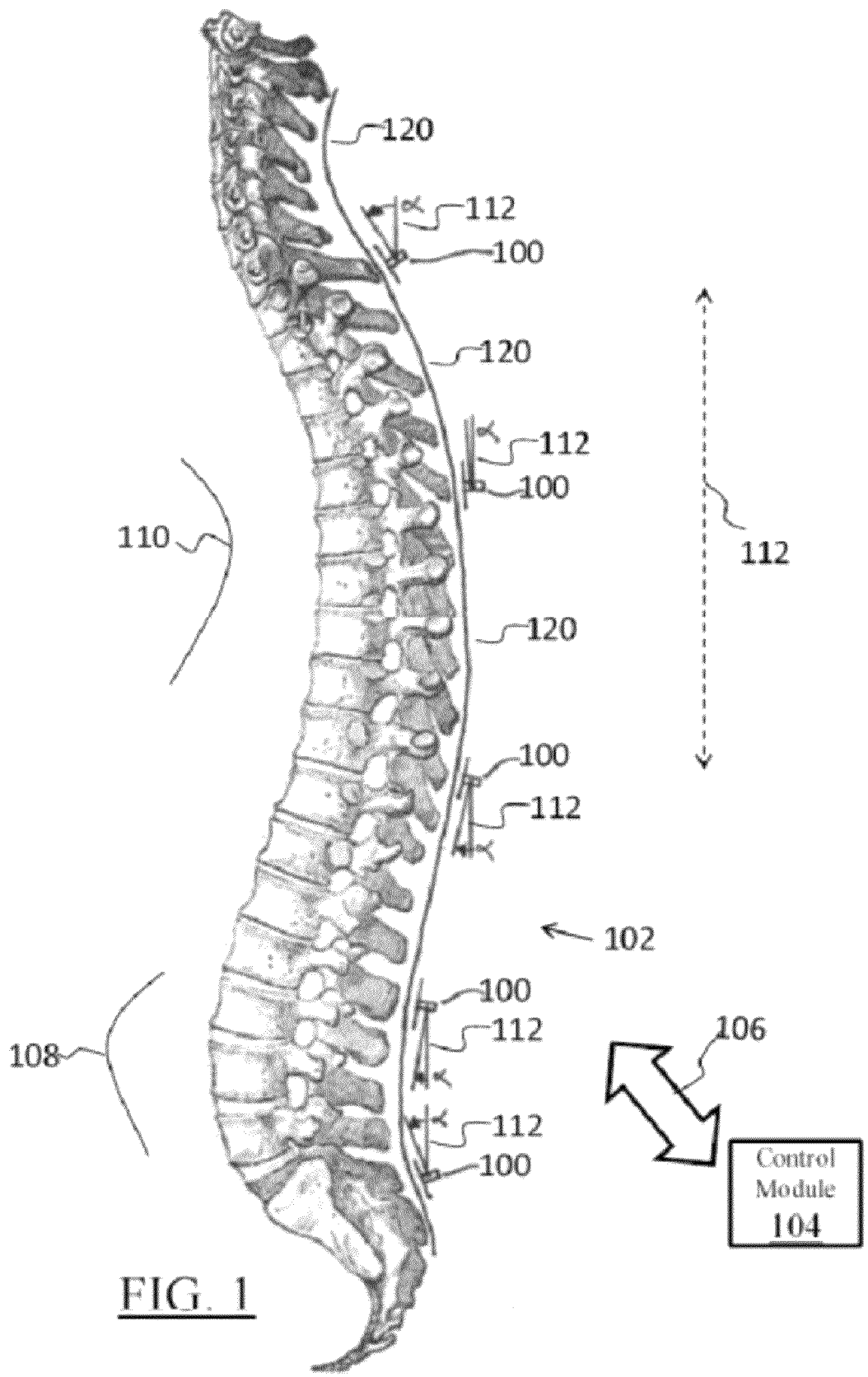
FIG. 1 is an exemplary illustration of the human vertebral column and associated sensory indication modules and a control module in accordance with the present invention.

The detailed description set forth below in connection with the appended drawings is intended as a description of presently preferred embodiments of the invention and is not intended to represent the only forms in which the present invention may be constructed and or utilized.

For purposes of illustration, programs and other executable program components are illustrated herein as discrete blocks, although it is recognized that such programs and components may reside at various times in different storage components, and are executed by the data processor(s) of the computers. Further, each block within a flowchart may represent both method function(s), operation(s), or act(s) and one or more elements for performing the method function(s), operation(s), or act(s). In addition, depending upon the implementation, the corresponding one or more elements may be configured in hardware, software, firmware, or combinations thereof.

For the sake of convenience and clarity, this disclosure defines the term posture as the body position as a whole at a given moment. Further, and also for the sake of convenience and clarity, this disclosure defines good posture as the proper or appropriate body position as a whole at a given moment for a given activity, such as proper posture for the exemplary, non-limiting activities of standing, sitting, walking, jumping, kneeling, or proper posture for various golf swings. It should be noted that references to human body and, in particular, human vertebra throughout the disclosure are meant as illustrative and for convenience of example, only. The present invention may be used for training proper posture for dogs or other animals, and may also be used for proper posture training for proper use of hands, arms, or legs for a particular activity and therefore, is not limited to humans or human vertebrae.

Most people by training or naturally perform an activity with the appropriate posture for that activity when they consciously realize that their body has an incorrect posture for the activity being performed. For example, most people naturally stand straight with a good posture when they consciously realize that their back is not straight. However, because of the countless daily distractions this awareness fades and the appropriate posture for the given activity gradually deteriorates. If not corrected, the bad posture worsens over time and may lead to permanent deformation of the spine and back pain in the exemplary instance of improper posture for the activity of standing, sitting, or the deterioration of performance of the activity (such as a poor golf swing due to improper posture).

With the present invention, users may orient (or position) their body to a proper posture for the given activity and save that proper posture as a preferred reference posture for that activity, with the present invention faithfully reminding users to always maintain the preferred posture if the body posture (position) deviates from it. For example, with the present invention users may stand naturally straight and save that posture as preferred reference posture for standing, with the present invention faithfully reminding them to always maintain the preferred reference posture if the body posture deviates from it. With regular use of the present invention, the users train the muscles to subconsciously hold that preferred reference posture, even after the present invention is no longer worn. With severe cases of deformity or a user new to a given activity, and with the supervision of a physician, a physical therapist, or a trainer, users may consciously work the specific muscles using the present invitation to incrementally and gradually correct their posture for the given activity. That is, in severe cases (or if the user is new to the activity) where the correction may be too drastic to achieve in one step, the present invention may be used to gradually correct and train for good posture for a given activity in multiple steps. At every step, the appropriate posture is saved and the muscles are gradually trained to finally achieve correct posture for the given activity.

The present invention provides a posture training device that corrects posture in relation to a reference. More specifically, the present invention provides a posture training device that corrects posture in relation to a true earth vertical. The present disclosure defines a true vertical direction as a direction locally aligned with the gradient of the gravity field, that is, with the direction of the gravitational force (per unit mass) at that point. The present invention uses small, lightweight accelerometers as angle sensors that simultaneously measure static angle relative to true earth vertical and acceleration in X, Y, and Z axis. The accelerometers used as angle sensors in accordance with the present invention accurately measure the acceleration of the earth gravity on a surface and, therefore, can measure angles relative to true earth vertical. Further integrated circuits are used that incorporate three accelerometers precisely positioned to measure angles and accelerations along three orthogonal axis, in the X (or forward-backward) and Y (or left-right inclination) from true vertical and Z (or up-down) accelerations. Accordingly, the present invention provides sensory indication modules that are intimately associated with a surface for detection of angles relative to true vertical and acceleration, and includes feedback indicators (stimulus or stimulation module) for communicating information in relation to the detected angles and acceleration of the surface with which the sensory indication modules are associated, with the user. The present invention combines the high performance accelerometers with algorithms and electronics to create a posture correction training device that is easy to wear on a daily basis and provides true posture correction for users for a given activity. The present invention further provides at least one control module for communicating command and control instructions with the sensory indication modules, including the activation of the feedback indicators (or stimulations) for correction of posture for a given activity. The present invention makes use of multiple feedback indicators (or stimulation mechanisms) that are placed at each measurement location to accurately alert users of the specific location of the body that needs correction for the given activity, and instructs the users with respect to the manner of correcting the posture.

FIG. 1 is an exemplary illustration of the posture training device associated with human vertebra, including a set of sensory indication modules and a control module in accordance with the present invention. As illustrated, the spine 102 relies on the natural lordodic 108 and kyphotic 110 curvatures as well as the true vertical 112 posture to comfortably bear the weight of the upper body. Any unnatural deviation from the true vertical 112 will cause the back muscles to compensate and unevenly bear a large amount of weight, resulting in chronic sharp back pain. The present invention intimately associates a number of sensory indication modules 100 with the illustrated vertebra 102 via a module support 120 for detection of angles α of a specified vertebra relative to the true vertical 112 and the acceleration of that particular vertebra, and includes feedback indicators (not shown in FIG. 1) for communicating information in relation to the detected angle and acceleration with the users. The number of sensory indication modules 100 may be varied, and should not be limited to the exemplary five sensory indication modules 100 illustrated. Further illustrated is a control module 104 for communicating via an appropriate communication protocol 106 command and control instructions with the sensory indication modules 100.

As exemplarily illustrated in FIG. 1, the sensory indication modules 100 are positioned on the users' back via the module support 120 along the length of the vertebral column 102. More specifically, the sensory indication modules 100 are associated with vertebrae in the thoracic, lumbar, and sacrum sections of a spinal column 102 for detection of angle and acceleration thereof. One or more sensory indication modules 100 are associated with upper, middle, and lower segments of the thoracic section of the spinal column 102. The upper, middle, and lower segments of the thoracic section of the spinal column 102 are respectively comprised of first through fourth, fifth through eight, and ninth through twelfth thoracic vertebra.

As further illustrated, each sensory indication module 100 is held against the user's back (via a module support 120) such that modules 100 are free to rotate with the vertebra directly underneath and report that particular vertebra angle in X, Y, and Z directions relative to true vertical. This unique combination of miniature sensors arranged in a line along the vertebral column 102 allows the accurate measurement of the angle of select vertebra in the vertebral column 102 starting at the top of the thoracic section or T1 vertebra, down to the pelvis. With the exemplary five sensor implementation the angles of T1, T5, T10, L2, vertebra and the pelvis (by way of the sacrum, which is attached to the pelvis) are measured. Of course, due to variability between users and in usage, the actual measurement points in terms of location and number of sensory indication modules 100 used will vary. This variation does not affect the functionality of the present invention, as described below. The analog signals representing the measured X, Y, and Z angles of accelerometer sensors (not shown in FIG. 1) of the sensory indication modules 100 are converted to digital form for digital processing in a microcontroller of the control module 104, and correction signals are communicated via the communication protocol 106 with the particular sensory indication module 100 that is associated with the specific vertebra. For example, vibration motors as the feedback indicators that may be incorporated inside each sensor indication module 100 may be used as one feedback method to alert or stimulate the users that the angle of a specific sensor is off and therefore the posture related to the specific vertebra needs to be corrected. Users may control the device of the present invention through an interactive unit (not shown in FIG. 1) that may be part of the controller module 104 or coupled through a wireless link with a Personal Digital Accessory, a cell phone, or other external device.

FIGS. 2A to 2D are an exemplary illustrations of a module support for facilitating the intimate association of the sensory indication module with a specific vertebra of a spine. Non-limiting examples of a module support 120 may include a garment 202 in the form an exemplary tight fitting undershirt (FIGS. 2A to 2D), a strap 302 (FIGS. 3A to 3D), or the like. Non-limiting examples of materials or fabric for the garment 202 or the strap 302 may include a blend of elastic, synthetic, and natural fibers, including lycra, spandex, polyester, cotton, or any combinations thereof, or the like. In fact, any material may be used so long as the module support 120 for the sensory indication modules 100 is tight fitting, flexible material that grips the body so that the sensory indication modules 100 are positioned close to the associated vertebra, but sufficiently flexible that would enable movement of the sensory indication modules 100 in relation to the movement of the spine 102. Stated otherwise, the alignment of the sensory indication modules 100 must closely conform to the contour of the spine 102. In addition, given their intimate physical proximity to human body, it is preferable if the sensory indication modules 100 and or the control module 104 are encapsulated within an entirely liquid impermeable material for safety. This way, the posture training device of the present invention may even be used by swimmers for training of appropriate posture for a given swim stroke.

As illustrated in FIGS. 2A to 2D, the sensory indication modules 100 may be intimately associated with vertebra 102 by connection to the module support 120 in the form of the exemplary garment 202, such as the illustrated tight fitting undershirt that may be worn by users. As exemplarily illustrated in FIGS. 2A to 2D, the sensory indication modules 100 are intimately associated with and aligned along the vertebra 102 to closely parallel and mimic angle and acceleration of the vertebra 102 during an activity. This way, the intimate physical proximity of the sensory indication modules 100 with the vertebra 102 enables the sensory indication modules 100 to be in sync with the angle and acceleration of the vertebra 102 for accurate reading of angles relative to true vertical, including acceleration thereof.

Figure 2A:
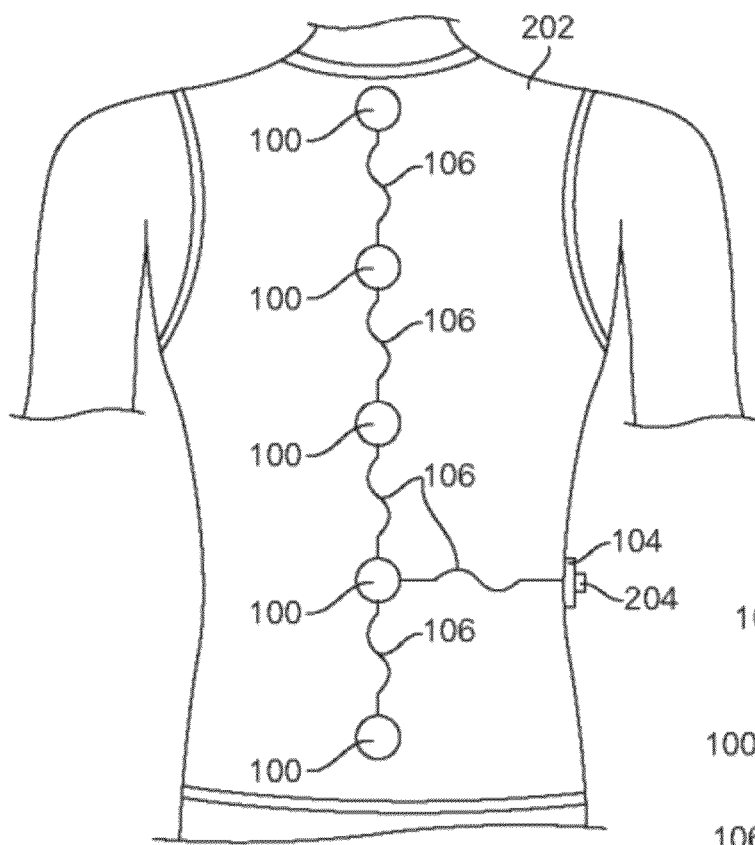
FIGS. 2A to 2D are an exemplary illustrations of a module support for facilitating an intimate association of a sensory indication module with a specific vertebra of a spine.
Figure 2B:
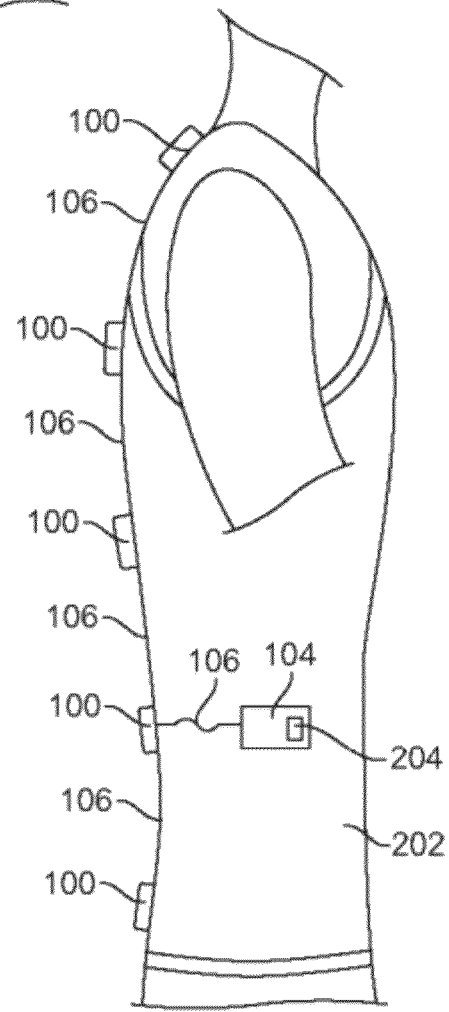
Figure 2C:
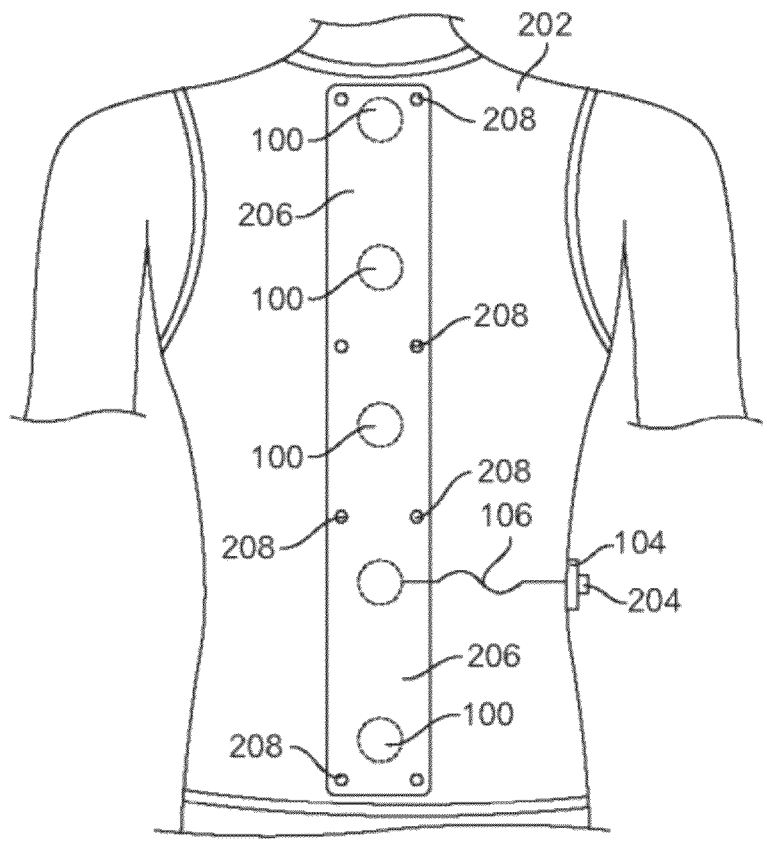

As best illustrated in the exemplary FIG. 2C, the module support 120 (in the form of the garment 202) may further include a cover 206 that covers the sensory indication modules 100 and interconnections (if wires are used), preventing the sensory indication modules 100 and the interconnections from snagging with other clothing. The cover 206 includes a set of cover fasteners 208 that coupled the cover 206 with the garment 202. The cover 206 may be comprised of the same fabric as the module support 120, placed over the sensory indication modules 100 and interconnections.

Figure 2D:
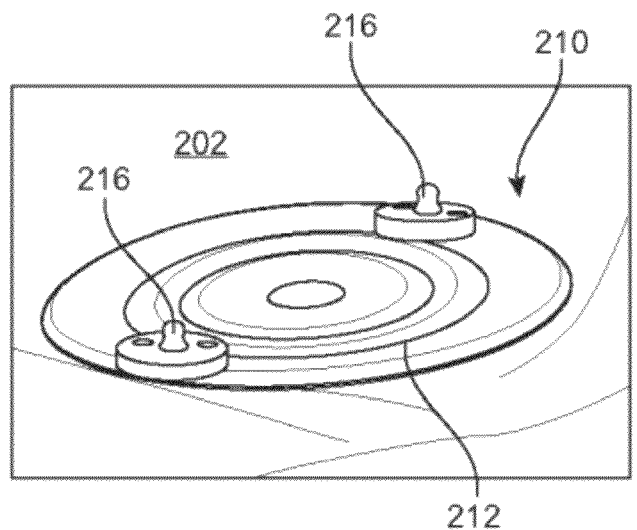

As illustrated in FIGS. 2A to 2D and, in particular FIG. 2D, the sensory indication modules 100 are detachably coupled with the back of the tight fitting garment 202 via a set of module support fasteners 210. The set of module support fasteners 210 may be coupled with the module support 210 by any well known manner, non-limiting examples of which may include sowing, use of glue or adhesive, etc., and aligned with an associated vertebra of the users. The spacing between the sensory indication modules 100 may vary, and depend on size of the module support 202 for enabling appropriate alignment of each sensory indication module 100 with an associated vertebra. That is, the position or placement of sensory indication modules 100 may vary commensurate with the size of the person, with each sensor independent of the other. This can be easily achieved by simply varying the location, placement, or spacing of the set of module support fasteners 210 along the back of the module support 120.

As best illustrated in FIG. 2D, the set of module support fasteners 210 on the module support 120 include a base portion 212 that is semi-rigid, which facilitates a better contact between the sensory indication modules 100 and the module support 202 when the sensory indication modules 100 are detachably mounted onto the set of module support fasteners 210. The base portion 212 provides a greater surface contact area with the flexible module support 120 underneath. That is, the base portion 212 widens the contacting surface area with the module support 202, and allows the detachably mounted sensory indication modules 100 to better follow the movement (angle) of the surface of the back, underneath. Non-limiting, exemplary set of module support fasteners 210 used may further include male snaps 216 protruded from the base 212 that can be used to detachably couple sensory indication modules 100 (that may have a corresponding set of female snaps). The set of module support fasteners 210 may comprise of any material, including plastics or electrically conductive material such as metal. The set of module support fasteners 210 may be such that the male snaps 216 thereon may provide power and communications signals between sensory indication modules 100, the control module 104, and other external devices. That is, the module support 120 may be wired (with or without embedded wiring) so that each module support fastener 210 can have an electrical/signal connection with other module support fasteners 210.

As best illustrated in FIG. 2B, the control module 104 may be coupled with the module support 120 in an appropriate or desired position similar to sensory indication modules 100. That is, both the sensory indication modules 100 and the control module 104 may include respective set of fastener mechanisms for detachable coupling the sensory indication modules 100 and the control module 104 with a module support 202. Alternatively, the module support 202 may include a compartment for housing the control module 104, which can be in the form of a pocket. As further illustrated in FIGS. 2A to 2C, the communication protocol 106 used between the sensory indication module 100 and the control module 104 may be in the exemplary form of electrical connections between sensory indication modules 100 and the control module 104 and be of a type of cable that uses a flexible jacket such as neoprene and carries individual stranded wires for added flexibility.

Figure 3A:
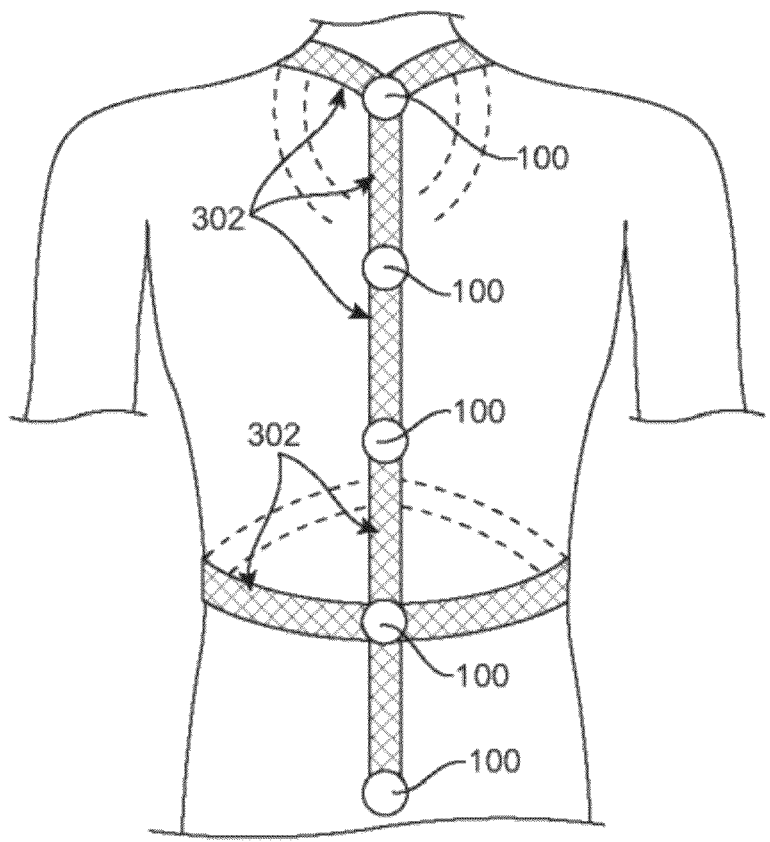
FIGS. 3A to 3D are an exemplary illustrations of another module support for facilitating an intimate association of a sensory indication module with a specific vertebra of a spine.
Figure 3B:
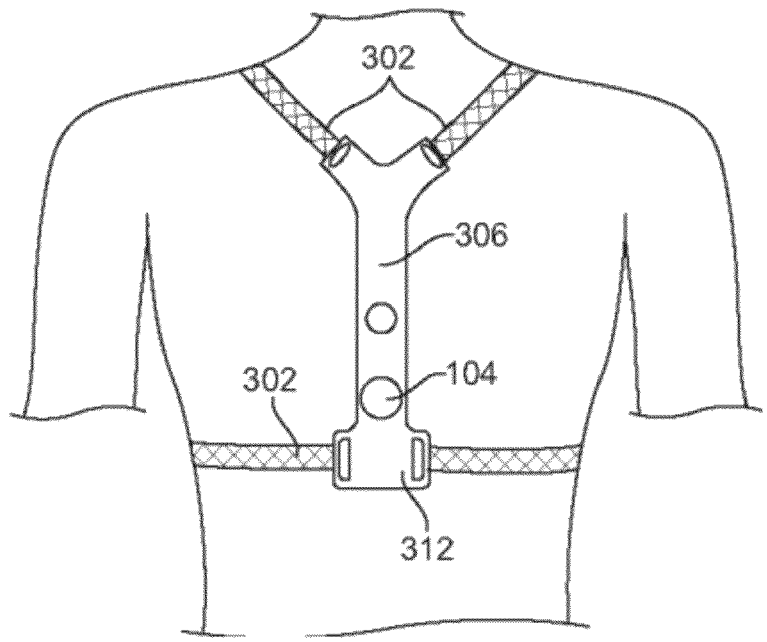

FIGS. 3A to 3E are exemplary illustrations of another module support for facilitating the intimate association of the sensory indication module with a specific vertebra of a spine. As best illustrated in FIGS. 3A to 3E, the module support 120 illustrated is in the form of an exemplary strap, suspenders, or elastic bands 302 that may include embedded wiring, just as the tight fitting garment 202. Sections of the elastic bands 302 (the strap—woven, knit or braided using natural and synthetic fibers) connect the sensory indication modules 100 together and hold them in place. Electrical wires 304 embedded inside the elastic bands 302 (FIG. 3D) carry power and data signals between all the sensory indication modules 100 and the control modules 104. This linear array of sensory indication modules 100 interconnected by thin, flexible and elastic bands 302 may comfortably be worn by users. As best illustrated in FIG. 3A (user back), FIG. 3B (user chest—front), and FIG. 3C (user profile), straps run over the shoulders on each side of the users and meet again at front (FIG. 3B) at a central semi-rigid polymer chest element 306 at the chest 308 of the user. Two additional elastic waist straps 302 are detachably coupled by a coupler 312 at the bottom of the chest element 306, wrapped around the waste and meet at the back (FIG. 3A), with a sensory indication module 100 located over the lumbar section.

The shoulder and waist straps 302 are adjustable using adjusters 310 to accommodate different size users and together with the chest element 306 hold the sensory indication modules 100 against the back along the natural kyphotic 110 curve of the thoracic vertebra. The sensory indication modules 100 located further down from the waist strap attachment point follow the natural curve of the lower back but may also rely on a tight fitting undershirt or garment to stay in place.

Figure 3E:
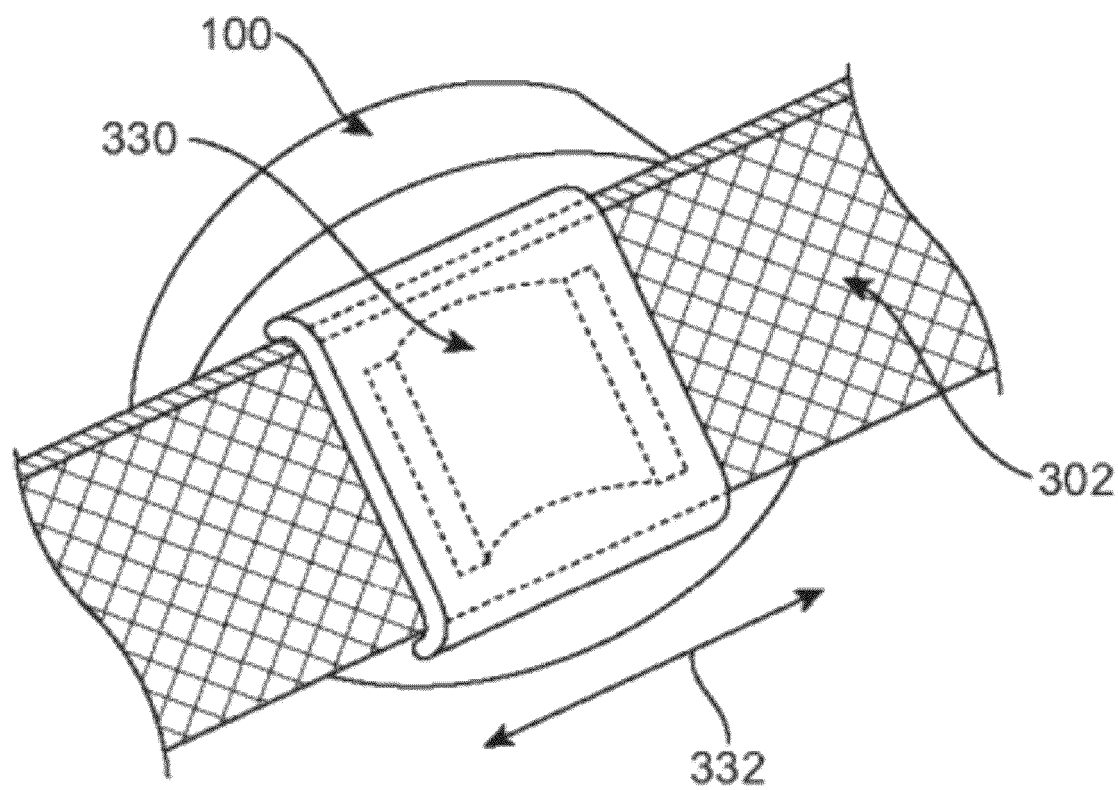

As further illustrated in FIG. 3E, in addition to adjusters 310 to enable adjustment of the strap in relation to a size of a users, the sensory indication modules 100 may further include sensory adjusters 330 to enable adjustment of the position of the sensory indication modules 100 along a reciprocating direction 332 on the strap 302. That is, sensory indication modules 100 can ride along the strap and can move along the strap length so that they can be aligned and adjusted using the sensory adjusters 330. Accordingly, the same size strap with adjusters 310 and the same number of sensory indication modules 100 can be manufactured in high volume to lower manufacturing costs, but still maintain the flexibility in terms of alignment of the sensory indication modules 100 along the strap, and hence, along the vertebra of different size users. As further illustrated, users control the posture training device of the present invention by the control module 104, which is incorporated inside the chest element 306 through an interactive unit 204.

Figure 4:
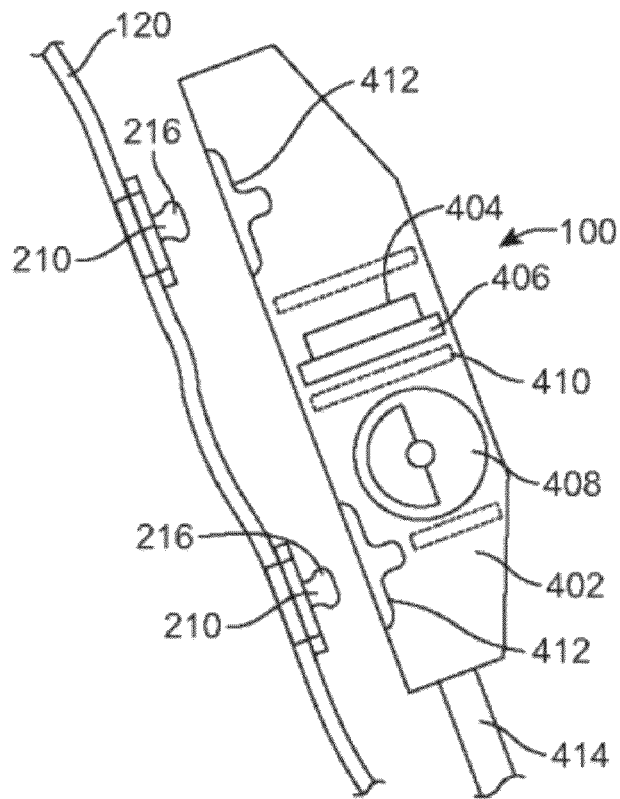
FIG. 4 is an exemplary illustration of an exemplary physical implementation of a sensory indication module in accordance with the present invention.

FIG. 4 is an exemplary illustration of a physical implementation of a sensory indication module in accordance with the present invention. As illustrated, the sensory indication modules 100 (including all internal components that are detailed below in relation to FIG. 7) are encapsulated within a soft casing 402, which makes touch of the sensory indication modules 100 against the skin or body of users comfortable. Non-limiting examples of materials for casing 402 may include a semi-rigid polymer resin.

As further illustrated in FIG. 4, the sensory indication modules may include exemplary fastener mechanism 412 included with the casing 402 that may be used to couple the sensory indication modules 100 with a corresponding set of module support fasteners 210 that include the exemplary set of male snaps 216. That is, the female snaps 412 of the sensory indication modules 100 snap onto the male snaps 216 that are coupled at appropriate locations on the module support 120. The set of module support fasteners 210 and the fastener mechanism 412 may be such that they may provide power and communications signals between sensory indication modules 100, the control module 104, and other external devices. It should be noted and apparent to those of ordinary skill that the number and the manner of coupling a sensory indication module 100 and a control module 104 with a module support 120 is too numerous to mention individually, and should not be limited to those illustrated and described.

As further illustrated, in this exemplary instance, the communications protocol 106 exemplarity illustrated as flexible wires 414 that connect the plurality of sensor indication modules 100 together and to control module 104. The exemplary wires 414 may carry power to the sensory indication modules 100 and communication data to the control module 104. In this exemplary instance, the power for the sensory indication modules 100 may be obtained from the control module 104, eliminating the need for a power source, which enables the true miniaturization of the sensory indication modules 100.

Internal the casing 402, the sensory indication modules 100 are comprised of the accelerometer sensors 404, the feedback indicator 408, and other components (described in detail below in relation to FIG. 7). The accelerometer sensor 404, the feedback indicator 408, and other components (detailed in FIG. 7 and described below) are positioned (mounted) on a single Printed Circuit Board (PCB) 406, which is supported by a frame 410. The frame 410 (which may be a housing) is generally comprised of a rigid resin with the PCB 406 mounted onto (or within) the frame 410. Accordingly, the main rigidity of the sensory indication modules 100 is within, which is a function of the frame (or internal housing) 410 of the modules 100. It should be noted that the present invention has a calibration and setting system (described below) that enable and can calibrate and set the perpendicular orientation of the sensors in relation to any surface to obtain the true vertical. Accordingly, the mounting orientation of the accelerometer sensors 404 in relation to the frame 410 may be varied.

Figure 5:
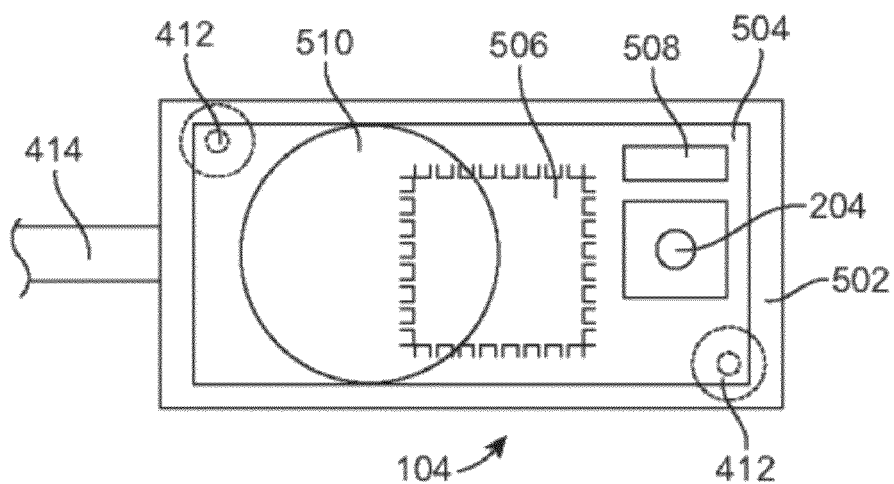
FIG. 5 is an exemplary illustration of an exemplary physical implementation of a control module in accordance with the present invention.

FIG. 5 is an exemplary illustration of a physical implementation of a control module in accordance with the present invention. As illustrated, the control module 104 is incased within a semi-rigid polymer resin controller encapsulation layer (or potting) 502. Although illustrated as an individual and separate module from the sensory indication modules 100, the control module 104 and at least one sensory indication module 100 may be combined into a single integrated unitary module. That is, one sensory indication module 100 can also include the entire control module itself as a single unitary module where that one sensory indication module 100 also functions as a control module in relation to the remaining sensory indication modules. In addition, the entire control module may be implemented into each of the sensory indication modules 100. That is, each sensory indication module 100 (and not just one) may include all the components of the control module 104. However, limitation for an integral, single unitary embodiment is the power source that would be required to power the components of the control module 104 and the individual sensory indication module 100. The use of power source will increase the size of each sensory indication module 100, making them somewhat impractical.

As further illustrated in FIG. 5, the control module 104 includes a Printed Circuit Board (PCB) assembly 504, with the PCB assembly 504 mounted inside a rigid polymer case, similar to frame 410 of the sensory indication modules 100. The PCB 504 includes various electronic and mechanical components that are part of the control module 104, the details of which are described below in relation to FIGS. 8 and 9. As illustrated in FIG. 5, the control module 104 includes a microcontroller 506 that manages the functionality of the entire unit, and communications unit 508 that enables the control module 104 to communicate with sensory indication modules 100 and other external devices. A power source 510 powers the control module 104 and the sensory indication modules 100, and may be in the form of a rechargeable battery that may be housed inside the control module 104, with a lid provided over the battery for easy replacement thereof. The control module 104 further includes an interactive unit 204 for activating the control module 104, setting references, and other functions, with the entire control module coupled with a module support 120 via the exemplary set of fastener mechanism 412.

Figure 6A:
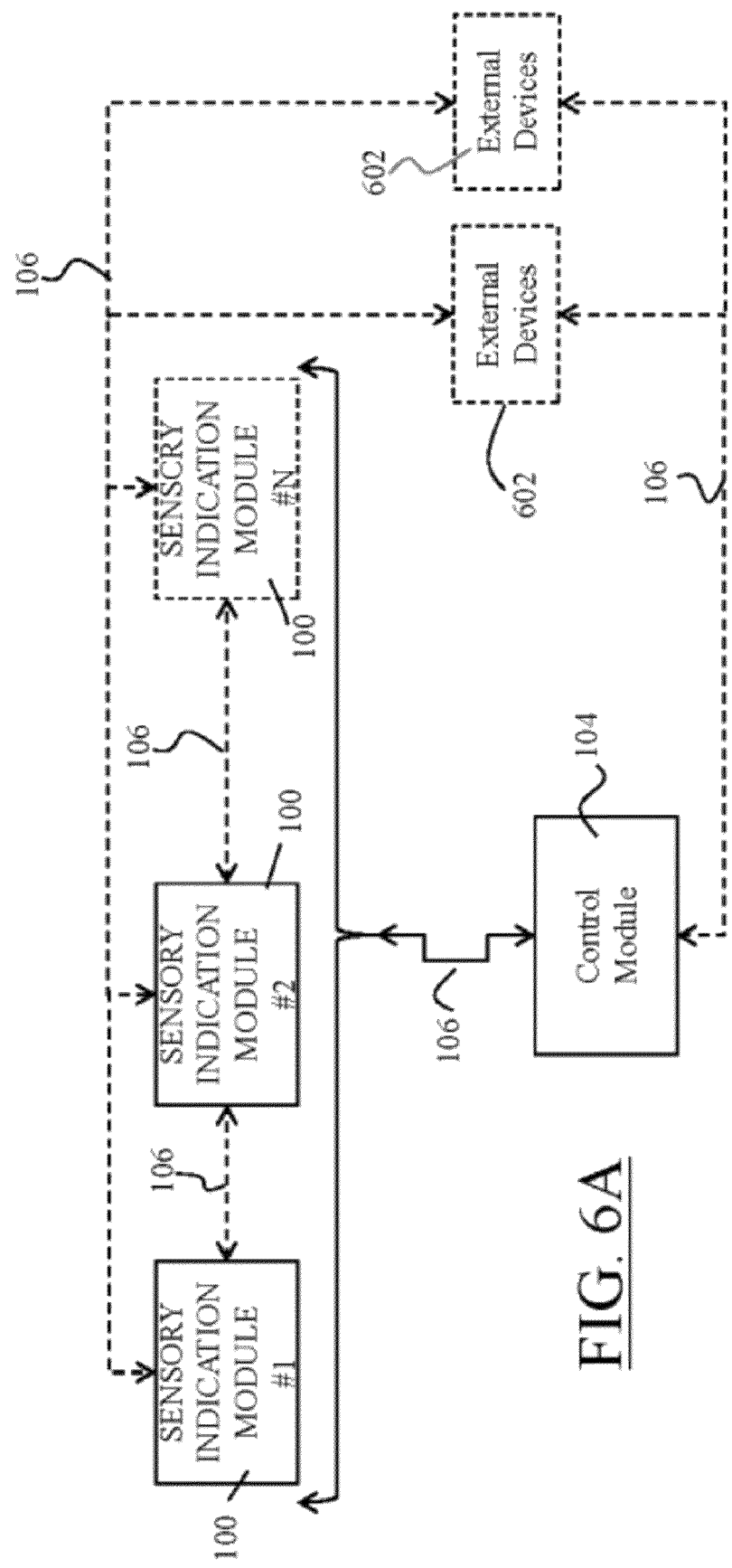
FIG. 6A is an exemplary, general, schematic overview illustration of the posture training device, including a sensory indication modules and a control module in accordance with the present invention.

FIG. 6A is an exemplary, general, schematic overview illustration of the posture training device, including the sensory indication modules and the control module in accordance with the present invention. As illustrated in FIG. 6A, any number of N sensory indication modules 100 may be used. Further, the sensory indication modules 100 may directly or indirectly (via the control module 104 and or one or more external devices 602) communicate with one another and also with the control module 104 using communications protocol 106. It should be noted that both the control module 104 and the sensory indication modules 100 include respective communication units that enables communication between both modules and external devices 602. Non-limiting examples of external devices 602 may include Personal Computers, PDAs, cell phones, etc. The communication between the modules may be by any appropriate communications protocol, direct or indirect, only limited by practical implementation of the device (e.g., size, power usage, etc.). That is, the modules are preferably small size, and use negligible power. Accordingly, the communication protocol adopted should not increase, but maintain the small size of the modules and use negligible power. Non-limiting example of communications protocols 106 may include wired (e.g., serial/parallel connectivity) or wireless (e.g., remote control, Bluetooth, Radio Frequency (RF), Infrared, cellular, PDA, LAN or WAN, Internet, or via a computer system (such as a server) or wireless network or any combinations thereof. For wireless communications, it is obvious that a transceiver is required in both of the modules (100 and 104), with the transceiver requiring power. Accordingly, the illustrated wiring 414 in FIGS. 4 and 5 above may be replaced by an appropriate communication protocol 106 that may be implemented as a wireless system. Regardless of the particular type of communications protocol 106 selected, it is preferred that the communication protocol 106 selected have small footprint and use negligible power for practical implementation of the system. The power for the sensory indication modules 100 may be independently provided (such as each module having a battery) or with power preferably provided to each sensor indication modules 100 by the control module 104.

Figure 6B:
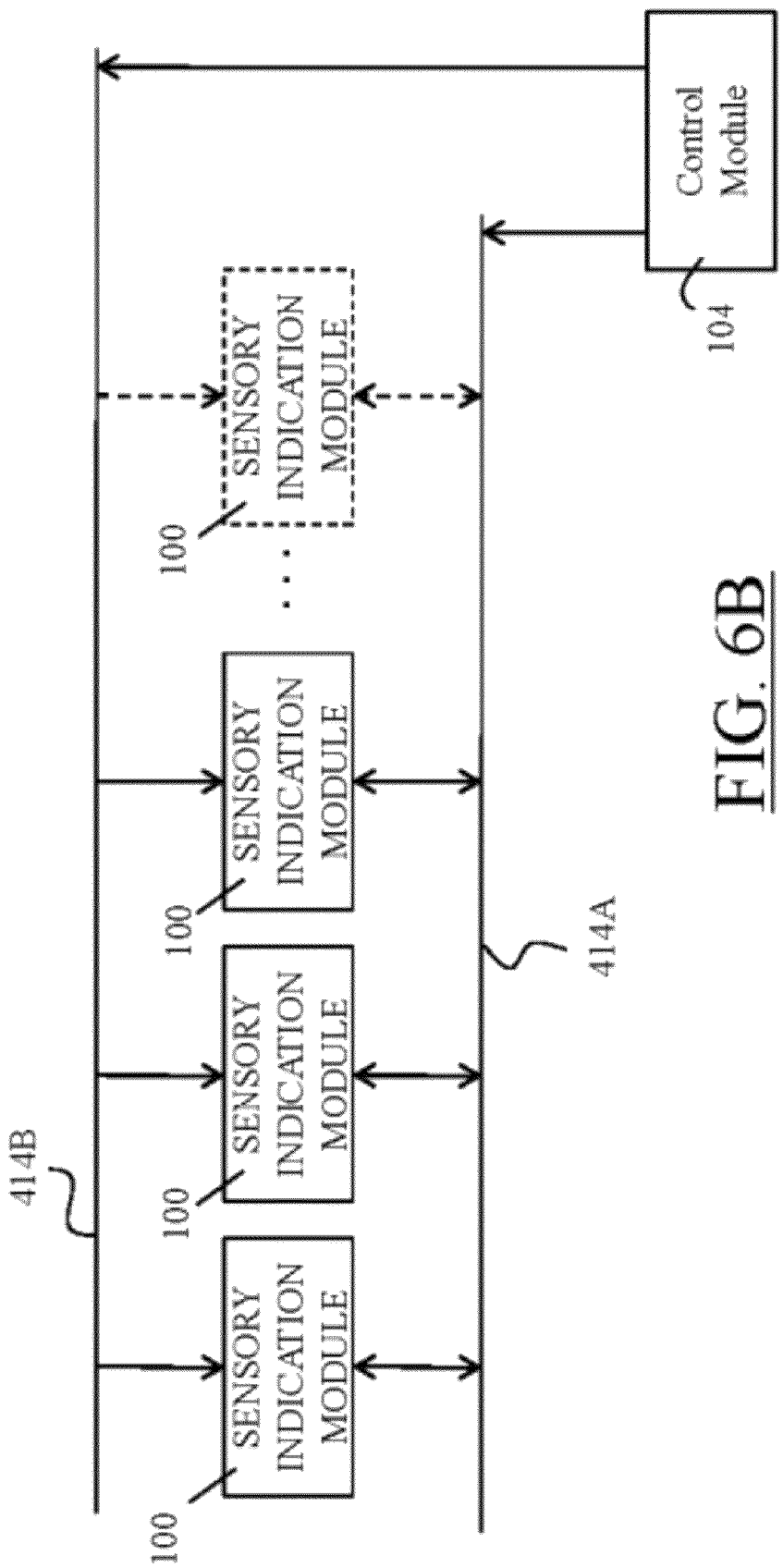
FIG. 6B is an exemplary schematic illustration of one specific implementation of the posture training device that is generally illustrated in FIG. 6A in accordance with the present invention.

FIG. 6B is a specific exemplary implementation of that, which is illustrated in general in FIG. 6A. That is, FIG. 6B exemplarily illustrates a set of sensory indication modules 100 that directly communicate with the control module 104 using a single wire serial bus topology 414A as the selected communications protocol 106, with power provided by a separate power bus 414B to the sensor indication modules 100 by the control module 104. A half-duplex master/slave type communication protocol is used to achieve two way data exchange between the sensory indication modules 100 and the control module 104 on the bus 414A. The control module 104 is the bus master and initiates all communication on the 414A. A sensory indication module 100 responds when it is specifically addressed by the control module 104. Through this network architecture, the control module 104 is able to get the angle data from all the sensory indication modules 100 using a single wire. This network also allows the control module 104 to send commands to individual sensory indication modules 100 on the same single wire, to turn on the feedback indicators (e.g., vibration motors). The single wire serial bus network 414A architecture also allows an RF link to be used for communication instead of a copper wire as an alternate implementation.

Figure 7:
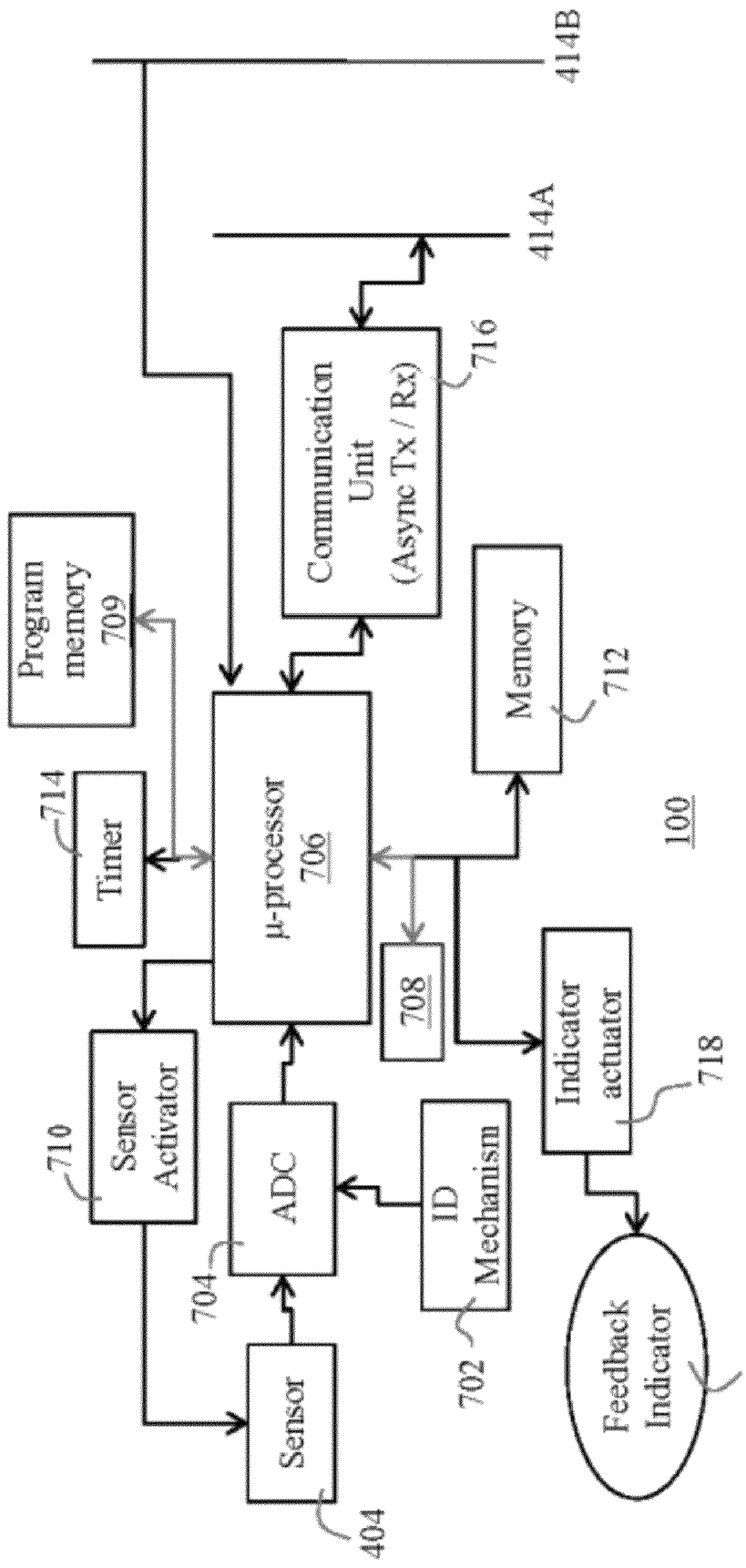
FIG. 7 is an exemplary schematic block diagram of a sensory indication module in accordance with the present invention.

FIG. 7 is an exemplary schematic block diagram of a sensory indication module in accordance with the present invention. As illustrated in FIG. 7, the sensory indication modules 100 includes an identification (ID) mechanism 702 for identifying a specific sensory indication module 100 by the generation of a unique analog ID signal. The ID mechanism 702 may be implemented as an impedance, non-limiting example of which may include a resistor. The use of an ID mechanism 702 allows all sensory indication modules 100 to use the same components, and be distinguishable by the generated unique analog ID signal. The ID mechanism 702 provides a specific signal/voltage level that identifies (or IDs) the sensory indication module 100 with which the ID mechanism 702 is associated. That is, the ID mechanism 702 is an impedance that generates the unique analog ID signal that identifies the sensory indication module 100 for unique association of the identified sensory indication module with a specific vertebra. This enables the sensory indication module to be uniquely associated with a specified vertebra, while making the components of all sensors identical, which lowers manufacturing costs. The use of the ID mechanism 702 also enables one sensory indication module to be distinguished from another sensory indication module, especially when they communicate on the same serial bus 414A with a control module 104 (in accordance with one implementation of the posture training device of the present invention illustrated in FIG. 6B). Accordingly, when the control module 104 receives signals from specific sensory indication modules 100, the control module 104 can determine which sensory indication module 100 forwarded the signal based on the generated analog ID signal of that sensory indication module 100. It should be noted that the ID mechanism 702 may be software based and/or set in software, rather than implemented as the illustrated hardware element (e.g., a resistor).

As further illustrated in FIG. 7, the sensory indication modules 100 further include the miniaturized multi-axis accelerometer sensor 404 for sensing (in the X, Y, and Z axis) the angle of the vertebra in relation to a true vertical and acceleration, and generating a first analog signal that includes information about the angle and the acceleration of that particular vertebra (in the X, Y, and Z axis) with which the sensory incitation module 100 is associated.

The accelerometer sensors 404 used in the sensory indicator modules 100 are well-known off-the-shelf products, non-limiting examples of which may include the use of accelerometer sensor ADXL335 from Analog Devices, details of which is provided in the iMEMES Accelerometer publication by Analog Devices. The accelerometer sensors 404 used by the present invention are miniaturized multi-axis accelerometers, built on a single Integrated Circuit, and can measure the static (tilt sensing) and dynamic (motion) accelerations, and have orthogonal sense direction with negligible cross-axis sensitivity—each axis (X, Y, and Z) is measured mutually exclusive of the other. The accelerometers can sense acceleration along multiple axes along the x—front/back, y—left/right, and z—up/down.

Accelerometers are used as angle sensors in accordance with the present invention because they can detect centripetal acceleration of the objects to determine their angular orientation in relation to the true vertical. The earth's rotation generates a centripetal force that acts at right angles in relation to the velocity of an object (which is tangential to the earth's surface), causing a continuous centripetal acceleration of objects towards the center of the earth. Accordingly, the centripetal acceleration/force and the velocity of the object are always perpendicular to one another. Therefore, the centripetal acceleration/force defines the true vertical orientation of the object, and the velocity, the true horizontal. An object's vertical orientation may be calibrated and measured by the centripetal acceleration/force of the earth on that object. If the object changes its orientation and deviates from the true vertical by some angle $\alpha$, the continuous centripetal acceleration/force experienced by the object at that new angle $\alpha$ will be different from the maximum (when the object is exactly tangent to the earth's surface) and this difference can be measured by the accelerometers (the static acceleration–tilt sense). The differences in the centripetal acceleration/forces can be used to determine the angle $\alpha$. Stated otherwise, variations in the centripetal acceleration/force of the object due to object's deviation from the vertical can be used to measure and determine the angles by which the object has deviated from the true vertical. Accordingly, the angular changes of an object are derived by measuring the variations of the centripetal acceleration/force on the objects using accelerometers.

Different reference postures can be set and stored in the apparatus so that they would detect inappropriate posture within the context of a variety of activities. For example, the reference for correct posture when standing up, may not be appropriate when lifting an object. Accordingly, for a weight lifting activity, the setting for correct posture for a weight lifter will be different compared with the setting for correct posture of golf swing for a golfer. The application is also extendable to all vertebrate animals. The fact that the sensors are miniaturized enables users to easily wear the device without discomfort. Finally, the present invention continuously monitors the acceleration levels of the surface under consideration in the Z (or up-down) axis and alarms users if the levels exceed a preset level, this prevents inadvertent damage to the spine, legs, or other body parts of users suffering from, for example, herniated discs or osteoporosis.

As further illustrated in FIG. 7, the sensory indication modules 100 further include an Analog to Digital Converter (ADC) 704 for digitizing the analog ID signal and the first analog signal for processing by a microprocessor 706. The microprocessor 706 initiates ADC conversions under software control, and reads the digital angle values when the conversions are complete. The microprocessor 706 operates under software control that is stored in the program memory 709, and includes a non-volatile memory 708 that may be part of the microprocessor 706 for saving user settings, and further works with a memory unit 712 for storing data and as work area for use by the microprocessor 706. Non-limiting example of the microprocessor 706 used may include FPGA (Field Programmable Gate array), EEPROM, Application Specific Integrated Circuit (ASIC), or most other general purpose processors. The microprocessor 706 can be any off-the-shelf processor that can perform the functions required by the present invention, using low power.

As further illustrated in FIG. 7, the sensory indication modules 100 include a sensor activation mechanism 710 for periodically activating (or providing power to) the accelerometer sensor 404 for detection. The microprocessor 706 turns the accelerometer sensor 404 ON through the sensor activation mechanism 710 and under software control for a duration for angle readings and turns accelerometer sensor 404 OFF when done to save power. A timer 714 is used for synchronization of various functionalities of the sensory indication modules 100, including determining the rate by which data is transmitted and received. The sensory indication modules 100 also include a communication unit 716 for communication of data with the microprocessor 706 and external devices 602 using any appropriate communication protocol 106.

The sensory indication module 100 also includes a feedback indicator 408 for communicating improper angular orientation of the vertebra with which the identified sensory indication module 100 is associated. The feedback indicator 408 may be a vibration mechanism such as a vibration motor, but it may also be an external device 206, such as a cell phone or any other device, separate and remote from the sensory indication modules 100. In other words, an angle may be sensed, and the feedback indicator 408 activated, with the feedback indicator 408 remote and away from the actual sensed location. Non-limiting examples of feedback indicators 408 may include mechanical devices, audio devices, visual devices, or any combinations thereof. In fact, any type of mechanism or device that can provide localized differentiated stimulation to inform users to correct their posture at the specific location, and that may be incorporated inside each sensor indication module 100 or as part of an external device 206 may be used. These feedback indicators (e.g., a mechanical device such as a vibration motor) are used as one feedback method to alert (e.g., by vibration stimulation) the users that the angle of a specific sensor is off and therefore the posture in that local surface area of the body with which the sensory indication module 100 is associated needs to be corrected. For example, if a specific vertebra of a user is tilted too much to the right for a given activity (e.g., golf swing), the specific feedback indicator (e.g., an audio sound) associated with that particular vertebra may be activated and if tilted too much to the left, another audio sound may be activated twice (or output a different audio signal), in a quick, sequential bursts, which is an indication to the user to correct posture by tilting to the right. These types of localized feedback stimulations inform the user that the posture for the given activity is incorrect, and further, inform the user to make the appropriate localized correction (such as tilting to the left for correcting posture that is tilted too much to the right side). This encourages users to use and exercise the specific muscles, resulting in a correct posture for the given activity even after the device has been removed. The feedback indicator 408 may be actuated by an indicator actuator 718 based on a command from the microprocessor 706. That is, the exemplary indicator actuator 718 may function as a switch and provides power to the feedback indicator 408. The microprocessor 706 turns the feedback indicator 4080N and OFF through the indicator actuator 718 and under software control as necessary to alert the user. It is preferred if the feedback indicators 408 are vibration devices because the users can instantly feel the exact location of posture requiring correction. It would be difficult for the user to "feel" the exact location with a flashing light or audio sound.

As further illustrated in FIG. 7, in this particular exemplary implementation illustrated in FIG. 7, the sensory indication module communication unit 716 is an exemplary asynchronous receiver transmitter. The asynchronous receiver transmitter allows the microprocessor 706 to receive commands from and send sensor angle data to the control module 104. The use of asynchronous system reduces the need for use of plurality of wiring, and enables the use of a single wire and/or single RF channel. It should also be noted that the respective data and power buses 414A and 414B illustrated may be combined into a single wire. This way, the data signals may be modulated onto the power signal. In this instance, a modulator/demodulator would be required to demodulate the data signal from power signal. Of course, asynchronous receiver transmitter may be replaced by an RF transceiver module or any of the above mentioned communication protocols 106, which may require independent power source (e.g., a battery) for each individual sensory indication modules 100.

In general, the microprocessor 706 is capable of operating in at least two power modes, which are running mode of operation and sleep mode (or power save mode of operation). In sleep or power save mode of operation, all devices inside the sensory indication modules 100 are turned OFF except the communications protocol unit 716, the exemplary asynchronous receiver transmitter. The microprocessor 706 stops all internal operations to minimize power drain. The sensory indication modules 100 remain in this mode until a command is received from the microcontroller 506 of the control module 104. Upon receipt of such command, the asynchronous receiver transmitter triggers the microprocessor 706 of the sensory indication modules 100 to power ON and switch to running mode. It should be noted that the microcontroller 506 of the control module 104 activates all sensory indication modules 100 (and their respective accelerometer sensors 404) together via the respective sensory indication modules sensor actuators 710. For this implementation illustrated in FIG. 1, an exemplary five sensory indication modules 100 are used that communicate with the control module 104 through the same communication protocol 106 (the exemplary single wire serial bus 414A). The ADC 704, actuators 710 and 718, asynchronous receiver transmitter 716, and the various elements illustrated in FIG. 7 may be separate, independent ICs or part of the microprocessor IC 706. It should be noted that each sensor assembly may be self contained. Therefore, each sensory indication module 100 may operate autonomously but communicate with a control module 104 or one another, eliminating all the cables between the sensors and to the control module 104.

Figure 8:
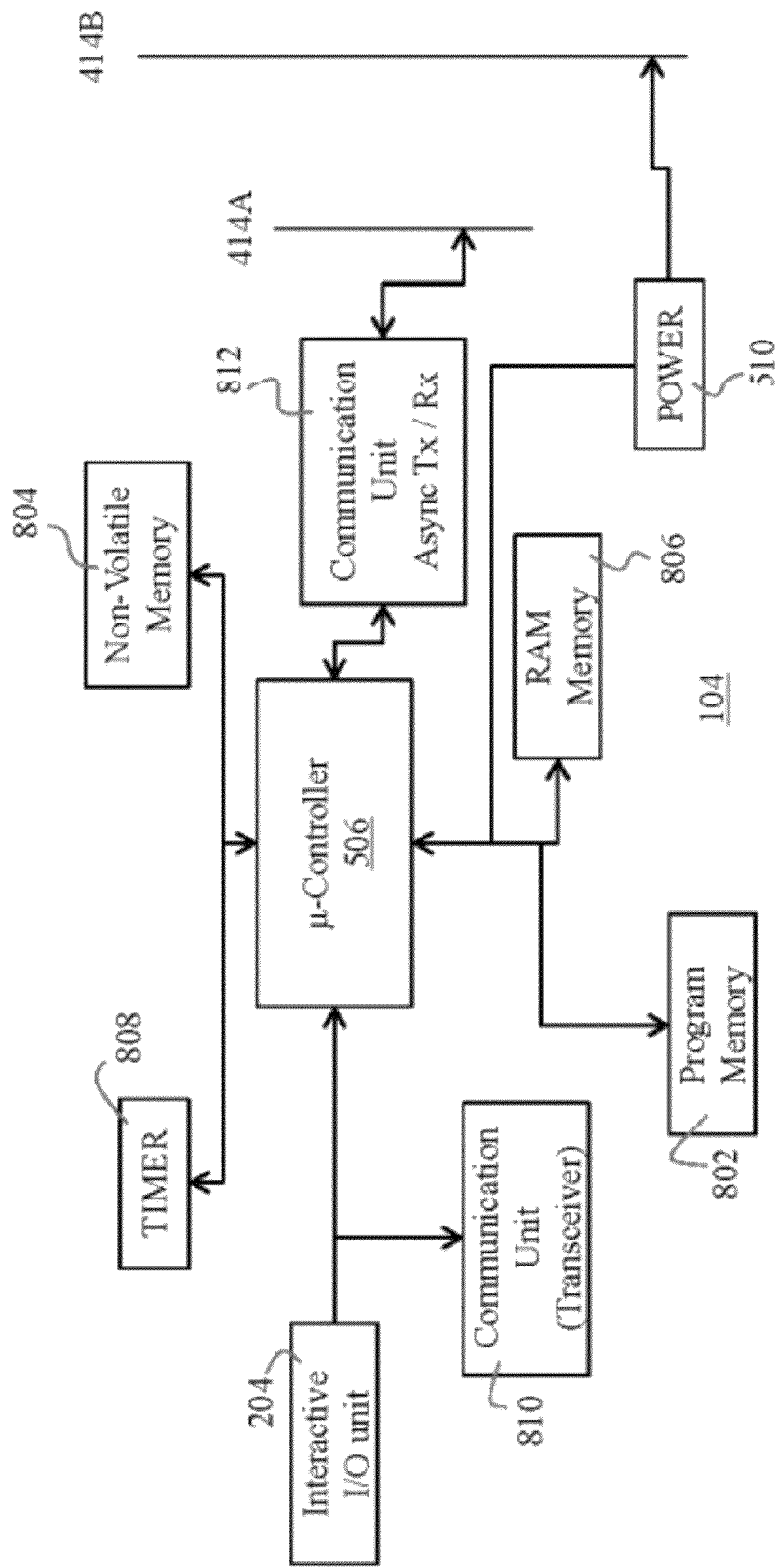
FIG. 8 is an exemplary schematic block diagram of a control module in accordance with the present invention.

FIG. 8 is an exemplary schematic block diagram of a control module in accordance with the present invention. As illustrated in FIG. 8, the control module 104 for communicating command and control instructions includes the interactive unit 204 for activating the control module 104 and for setting references. Non-limiting examples of the interactive unit 204 may include one or more simple push button switches, a touch screen display with various soft-action button icons for performing different functions (e.g., a set references icon, turn ON device icon, turn OFF device icon, etc.). Other non-limiting examples of an interactive unit 204 may include remote actuators, a cell phone, a PDA, or any type of input/output (I/O) device(s) that enables human interaction with the control module 104, and may be remote and physically separate from the control module 104.

The control module 104 also includes a microcontroller 506 with an associated program memory 802 having fixed set of instructions for the functionality of the microcontroller 506, a non-volatile memory 804 that may be used to save information such as user preferences, etc., and a Random Access Memory (RAM) 806 used by the microcontroller 506 for calculations and as a work area. Non-limiting example of the microcontroller 506 used may include Field Programmable Gate array, EEPROM, Application Specific Integrated Circuit (ASIC), or most other general purpose processors. In fact, any type of off-the-shelf microcontroller that can perform the functions required by the present invention may be used. The microprocessor 706 of the sensory indication modules 100 and the microcontroller 506 of the control module 104 may be identical, however, it is preferred that both consume low power.

As further illustrated in FIG. 8, the control module 104 further includes a timer 808 that may be used to wake up the microcontroller 506 itself from its sleep or power save mode. As will be described below, the duration of time for power save mode or full power ON mode is adaptive and varies depending on type of the signal received from sensors. For example, if the type of signal received is normal (the user has maintained perfect posture), the wakeup call will be less frequent. If the type of signal received is not normal (e.g., there is an angular deviation sensed by the sensory indication modules 100), the wake up calls will be more frequent for corrections. The adaptive scheme described further below in relation to FIGS. 10A to 11D is implemented to further save power usage.

As further illustrated in FIG. 8, the exemplary control module 104 further includes a transceiver 810 that enables communications between the microcontroller 506 and an external device 602. Further, an Asynchronous Receiver and Transmitter peripheral device 812 allows the control module 104 to communicate with the sensory indication modules 100 over the Single-Wire Serial Bus 414A. The control module 104 uses the Asynchronous Receiver and Transmitter 812 to send commands to, and receive data from the sensory indication modules 100 on the bus 414A. Of course, the transceiver 810 and the Asynchronous Receiver and Transmitter peripheral device 812 (individually or combined into a single communication unit) may be implemented using any appropriate communication protocol 106.

The control module 104 illustrated in FIG. 8 also provides the power source 510 (e.g., rechargeable battery) to power the control module 104, sensory indication modules 100, and or possibly other external devices 602. Although not illustrated, instead of having separate modules 100 and 104, a single unit may include the combined sensory indication module 100 and the control module 104 (combining FIGS. 7 and 8). In addition, the entire control module 104 may be implemented into each of the sensory indication modules 100. That is, each sensory indication module 100 may include all the components of the control module 104. In instances of combining the modules 100 and 104, all redundancies may be eliminated, including, for example, the use of only a single processor for the entire unit and so on.

Figure 9:
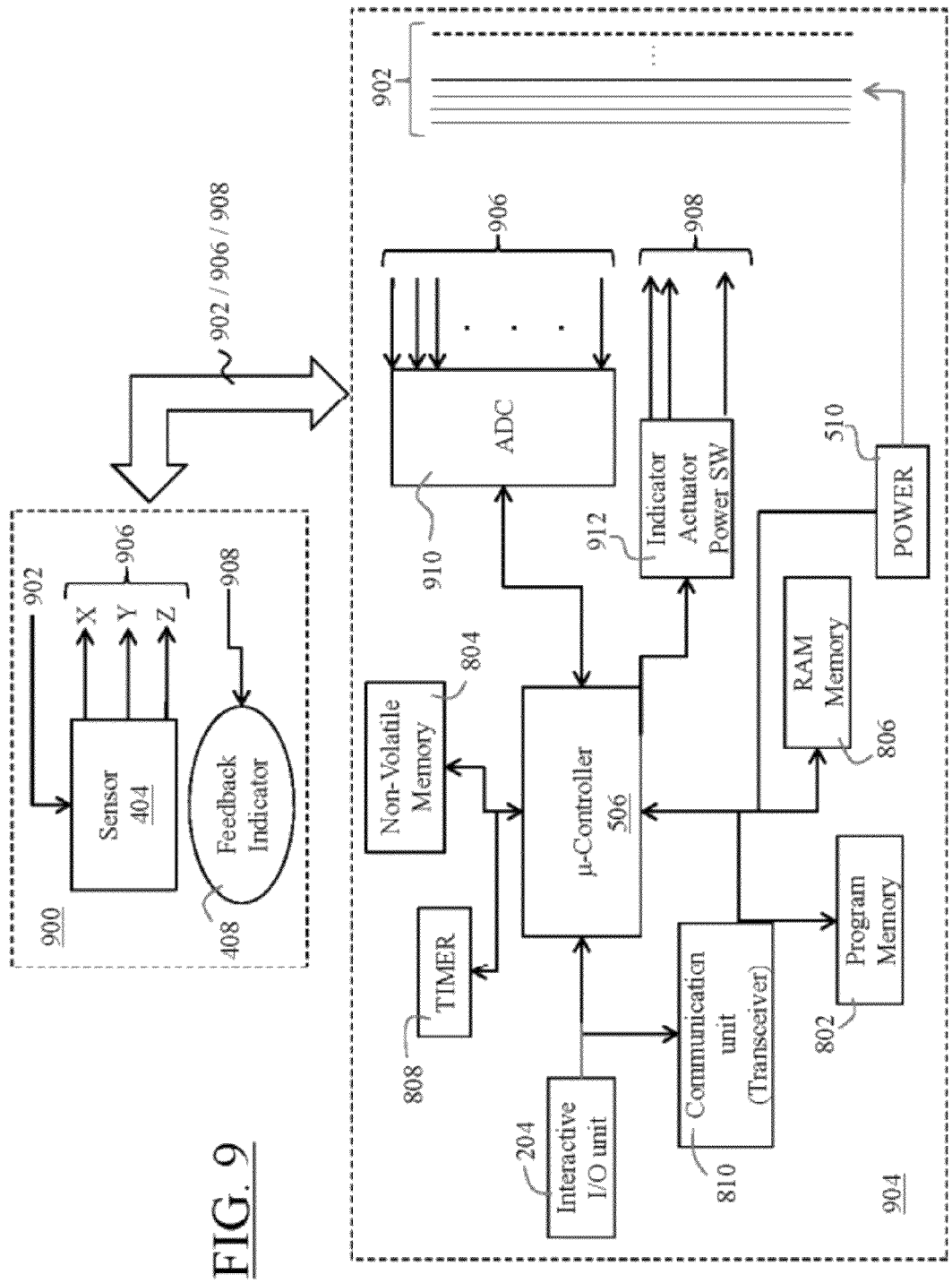
FIG. 9 is an exemplary schematic block diagram of another sensory indication module and control module in accordance with the present invention.

FIG. 9 is an exemplary schematic block diagram of the circuitry components of another sensory indication module and control module in accordance with the present invention. The sensory indication module 900 and the control module 904 include similar corresponding or equivalent components, interconnections, and or cooperative relationships as the sensory indication modules 100 and the control module 104 that are shown in FIGS. 1 to 8, and described above. Therefore, for the sake of brevity, clarity, convenience, and to avoid duplication, the general description of FIG. 9 will not repeat every corresponding or equivalent component and or interconnections that has already been described above in relation to sensory indication modules 100 and the control module 104 that are shown in FIGS. 1 to 8.

As illustrated in FIG. 9, in this alternate implementation, the sensory indication modules 900 only houses an accelerometer sensor 404 and a feedback indicator 408. With this implementation, the sensory indication modules 900 are also intimately associated with vertebra 102 for detection of angle and acceleration of vertebra, but only include an accelerometer sensor 404 for sensing (in X, Y, and Z axis) the angle of the vertebra and acceleration in relation to a true vertical, and generate a first analog signal 906 in the X, Y, and Z directions. Further, the feedback indicator 408 for communicating improper angular orientation of the vertebra with which the identified sensory indication module 900 is associated with the user is also provided. In this implementation, a control module 904 for communicating command and control instructions with the sensory indication modules 900 is provided. The X, Y, and Z angle analog output signals 906 are brought to a multiple input ADC 910 inside the control module 904 via a direct coupling, with power actuators 912 inside the control module 904 driving each feedback indicator 408 through an individual connection 908 to each sensor indication module 900.

As has been described, the posture training device of the present invention is most effective when worn by users throughout the duration of an activity. Users wear the posture-training device first, and then put on the rest of their activity attire that will be worn for duration of usage of the device. Users actuate the interactive unit 204 to turn ON the sensory indication modules 100. At power ON, all of the feedback indicators 408 (e.g., a vibration motor) may become active sequentially and output a stimulation (e.g., vibration of the motor in short repetitive bursts) to let the user know that the sensory indication modules 100 are ready and waiting to set the user preferred reference posture. This also indicates that all the feedback indicators are operating properly. To set the user preferred reference posture, users position their posture (hands, back, arms, etc.) in an orientation most appropriate for the particular activity for which they intend to perfect. For example, for the activity of standing, users may stand with the correct back posture and actuate the appropriate interactive unit 204 (e.g., press a push button for a certain duration, use a touch-screen, or by some other mechanism) to commence setting of reference. This saves the correct posture as the user preferred reference posture in the control module 104. Once a preferred reference posture is set, the feedback indicators 408 deactivate (e.g., the vibration motor or LED lights, or audio sounds are turned OFF) and the accelerometer sensors 404 commence monitoring the user's posture continuously.

If the user's posture deviates from the saved preferred reference posture by more than a set range (non-limiting example of which may include, e.g., ±3 degrees) the feedback indicator 408 inside the sensory indication modules 100 that detected the deviation will alert the user to correct posture. For example, the alert may include one short burst of vibration from an exemplary vibration motor to alert the user to correct in, for example, the backwards direction. Other types of alerts (e.g., two short bursts of vibration using the vibration motor) may be used to inform the user to correct posture in the forward direction. A completely different type of alert, such as a long burst of vibration may be used to alert the user if the deviation is in either left or right direction. In other words, various types of feedback stimulations may be used and may be associated with a specific type of correction to inform the user to make the appropriate correction. When the user corrects his or her posture in that localized area where incorrect posture was sensed, the indicator alerts stop. If more than one sensor detects a deviation, it is preferred that the indicator 408 in the uppermost sensory indication modules 100 that detected the deviation be activated first. Once that particular area has been corrected, the lower sensory indication modules 100 can then activate their respective indicators 408, if they continue to detect a deviation. This encourages the user to correct his or her posture from the top to down, which is applicable in most instances. Of course, the manner and the sequence of activating feedback indicator may be varied in accordance with the activity, and should not be limited to the top-down approach. The sensory indication modules 100 may be deactivated by actuating the interactive unit 204.

As is described further below in relation to FIGS. 10A to 11D, digital differentiation and integration algorithms performed by the microcontroller 506 under software control monitor the accelerometer sensor 404 outputs over time and determine the states or conditions during which it is not desirable to alert the user even though his or her posture may be off from the preferred reference posture. For this implementation, these conditions may include high acceleration levels which translate to the user walking or performing physical activity for which the posture training device was not set, and high angle deviations from true vertical that translate to the user either lying down or in a position not desirable for posture correction (e.g., bending to pickup an object).

The microcontroller 506 saves the preferred reference posture internally in non-volatile memory 804. Therefore, the same preferred reference posture can be recalled even after power down or battery change. When turning ON the sensory indication modules 100, the user may actuate the interactive unit 204 (which may include a soft-button icon that is dedicated for a recall function) to recall the last saved reference posture. Due to day to day variability in sensor position, clothing worn over the sensors, and physical changes of the user over time, regularly saving the reference posture may be desired.

Figure 10A:
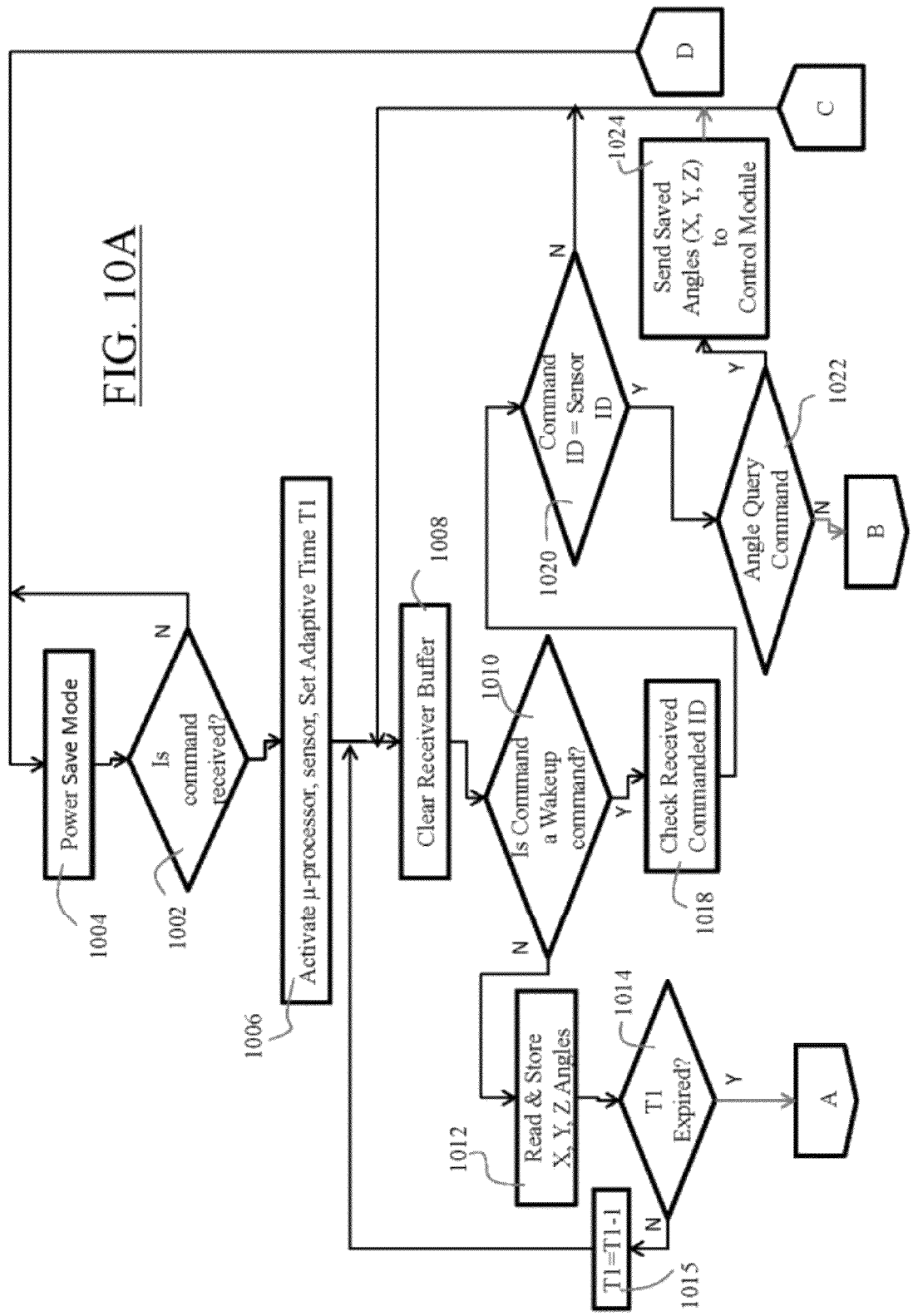
FIGS. 10A and 10B are exemplary flow diagrams of the functionality of the sensory indication modules in accordance with the present invention.
Figure 10B:
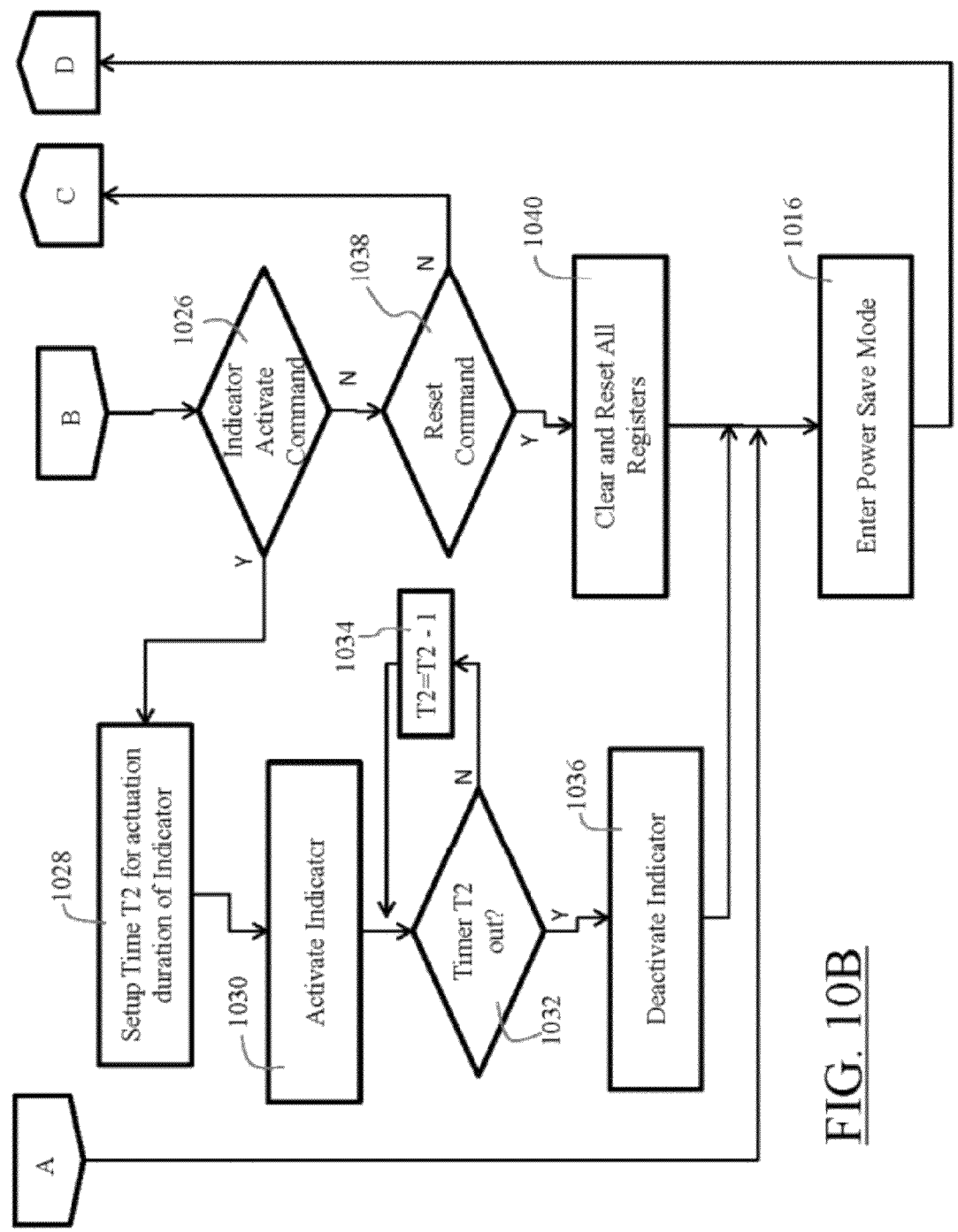

FIGS. 10A and 10B are exemplary flow diagrams of the functionality of the sensory indication modules in accordance with the present invention. Since the same sensory indication module code runs on all the sensory indication modules 100, this description applies to all the sensor indication modules 100 that are attached to the system network (e.g., using the communication protocol 106 described in FIG. 6B, which is the single wire serial bus). As described in relation to FIG. 7, each sensory indication module 100 however, is assembled with a different ID value for identification (by the ID mechanism 702) such that on power up, the microprocessor 706 reads the ID signal value and configures itself with a unique sensor address that corresponds to the physical position of the sensory indication module 100 on the user.

Each microprocessor 706 remains in the sleep mode the majority of the time. When entering this mode, the microprocessor 706 shuts down all devices, stops its internal clock, and halts all processing. In this state, the microprocessor 706 and the entire sensory indication module 100 draw negligible power and thus allows the entire device to run on very little power, for example, using a single coin type lithium battery for an extended period of time. While in this low power state however, specialized circuits inside the microprocessor 706 monitor the network line (e.g., bus 414A). Any activity on the network line triggers the microprocessor 706 to start its internal clock again and resume processing. The source of the network line activity comes from the control module 104, which deliberately toggles the network line periodically to turn ON all the sensory indication modules 100 and collect angle data or command a feedback indicator 408 to turn ON.

The control module 104 waits a short time after toggling the network line to allow all the sensory indication modules 104 to power ON, read the sensors, and be ready to receive commands. In general, the commands may be any length (byte size), with a few bytes or bits representing the destination sensory indication module 100 and others representing the command type. When the control module sends a command it is received by all sensory indication modules 100. Each sensory indication module 100 compares the sensor address in the received command with its own. If the sensor address doesn't match, it ignores the command. Therefore, while all sensory indication modules 100 receive the same command, only the intended sensory indication module 100 will respond to the control module.

As illustrated in detail in FIGS. 10A and 10B, at the operational act of 1002 the microprocessor 706 of the sensory indication modules 100 periodically determines if there is a command from a microcontroller 506 of the control module 104. If the microprocessor 706 determines that there is no command from the microcontroller 506 of the control module 104, the microprocessor 706 reverts back to sleep mode at operational act 1004. If the microprocessor 706 determines at the operational act 1002 that there is a command from the microcontroller 506 of the control module 104, the microprocessor 706 at the operational act 1006 is fully activated, which, in turn, activates the accelerometer sensor 404 for a first adaptive time period T1, and at the operational act 1008 clears the receiver buffer from all previously received commands (within a communications unit, such as the asynchronous transmitter receiver 716).

At operational act 1010 the microprocessor 706 determines if the command received from the microcontroller 506 is a wakeup command. If so, the microprocessor 706 reads and saves the detected angles (in the X, Y, and Z axis) of the vertebra by the accelerometer sensor 404 at the operational act 1012, and determines if the first adaptive time period T1 has expired at the operational act 1014 and 1015.

If the microprocessor 706 determines that the first adaptive time period T1 has expired at the operational act 1014, the operational act 1016 is executed wherein the posture training device is entered into a low power sleep mode by the microcontroller 506 of the control module 104. If the microprocessor 706 at the operational act 1014 determines that the first adaptive time period T1 has not expired, the receiver buffer is cleared (within communications unit such as the asynchronous transmitter receiver 716), and the operational act 1010 is executed again where the microprocessor 706 determines if the command is a command other than a wakeup command (e.g., a new command is received from the microcontroller 506 during the first adaptive time period T1 duration).

If the microprocessor 706 at the operational act 1010 determines that a new command is received (that is not a wakeup command) from the microcontroller 506, the microprocessor 706 at the operational acts 1018 and 1020 checks the received command ID to determine if the received new command from the microcontroller 506 is intended for the sensory indication module 100 to which the received command is sent. That is, the commands from the microcontroller 506 include ID tags that must match the ID signal output from ID mechanism 702 of the sensory indication modules 100. If the microprocessor 706 at the operational act 1020 determines that the command received from the microcontroller is intended for the sensory indication module to which the command is sent, the microprocessor 706 at the operational act 1022 determines if the command received is an angle query command; otherwise, the receiver buffer is cleared at the operational act 1008. If the microprocessor 706 at the operational act 1022 determines that command received is an angle query command, the microprocessor 706 at the operational act 1024 sends the saved sensed angular orientations to the microcontroller 506 or other external device 602 via an appropriate communications protocol 106, and the receiver buffer is cleared at the operational act 1008. However, if the microprocessor 706 determines at the operational act 1022 that command received is not the angle query command, the microprocessor 706 at the operational act 1026 determines if the command received is a command to activate a feedback indicator 408. As stated above, feedback indicators 408 may be activated for a number of reasons such as setting a reference posture, correction of posture, indicating that the sensor is active, and so on. If the microprocessor 706 determines that command received is a command to activate the indicator 408, a second duration T2 (where T1 is much greater than T2) is set for activation of the feedback indicator 408 at the operational act 1028, the feedback indicator 408 is activated for the second duration T2 at the operational act 1030, and the microcontroller 506 enters the entire apparatus into a low power sleep mode at the operational act 1016 after the second duration T2 has expired (determined by the operational acts 1032 and 1034) and the feedback indicator 408 is deactivated (at operational act 1036). On the other hand, if the microprocessor 706 determines at the operational act 1026 that command received is not a command to activate the feedback indicator 408 (e.g., posture is correct and no need for feedback stimulation), the microprocessor 706 at the operational act 1038 determines if the command received is a reset command. If so, the microprocessor 716 clears and resets all registers at the operational act 1040, and the microcontroller 506 enters the apparatus into a low power sleep mode at the operational act 1016.

Figure 11A:
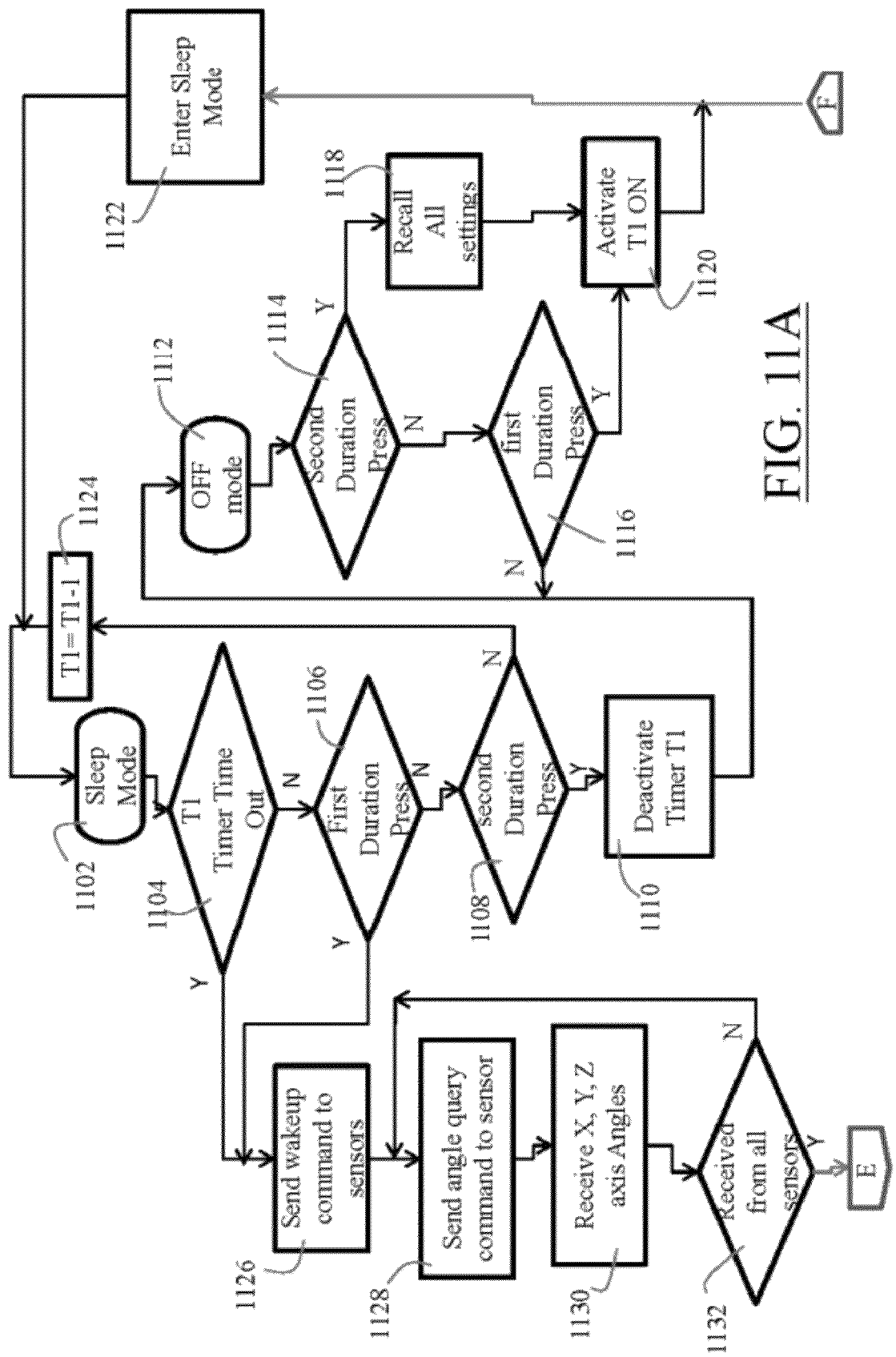
FIGS. 11A to 11D are exemplary flow diagrams of the functionality of the control module in accordance with the present invention.
Figure 11B:
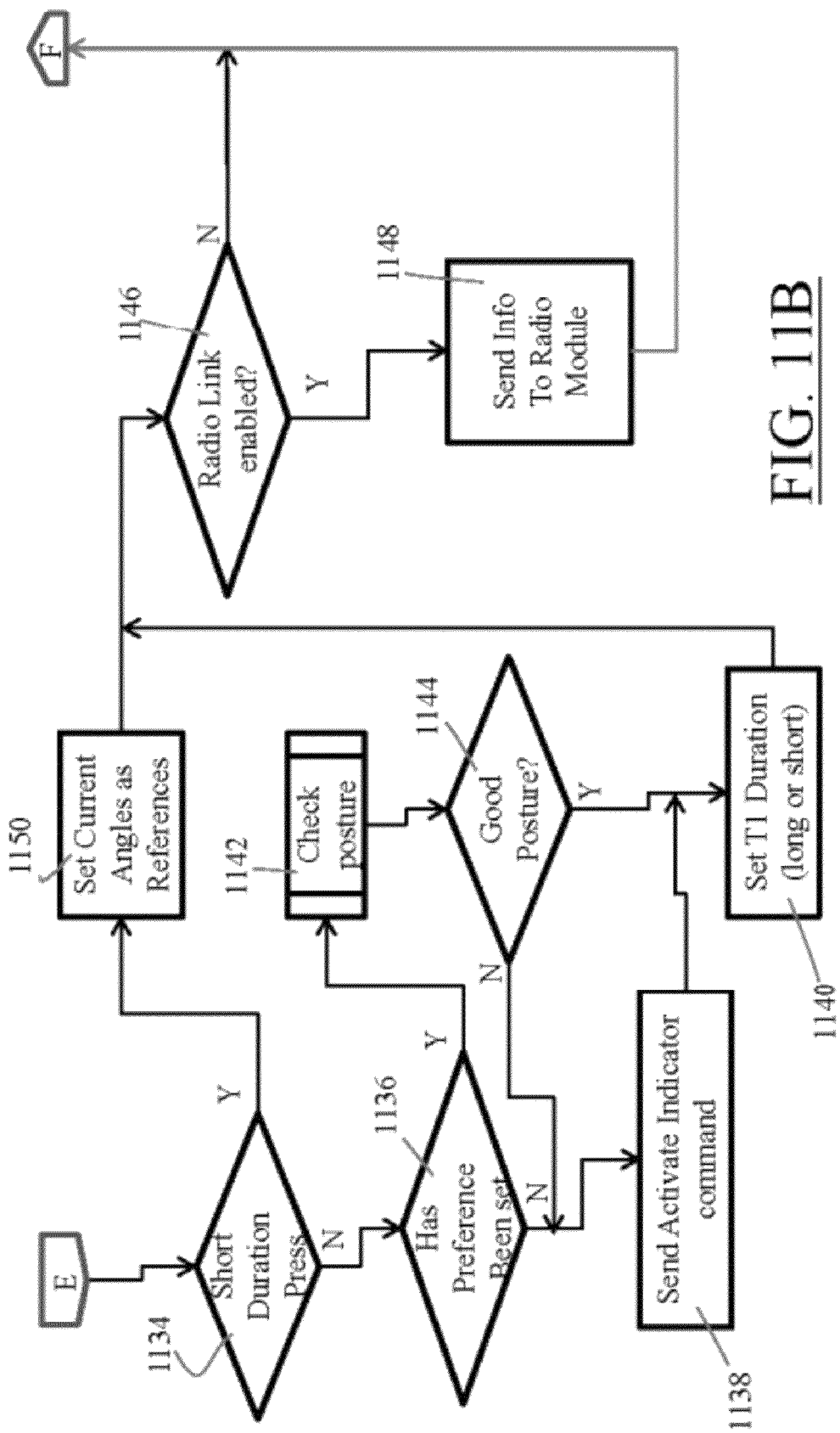

FIGS. 11A and 11B are exemplary flow diagrams of the functionality of the control module in accordance with the present invention. In general, the microcontroller 506 within the control module 104 remains in the sleep mode the majority of the time. When entering this mode, the microcontroller 506 shuts down all devices and halts all processing. In this state, the control module 104 draws negligible power and thus allows the entire device to run on very little power, for example, using a single coin type lithium battery for an extended period of time. While in this low power state, however, a timer inside the microcontroller 506 remains ON and continues to count and keep time. The microcontroller 506 programs a short or long delay in this timer before entering sleep mode.

While in sleep mode the timer 808 counts the programmed delay until it times out at which time it triggers the microcontroller 506 to power up again and resume processing. Once out of sleep mode the control module 104 in turn toggles the network line (e.g., line 414A) to force the sensory indication modules 100 ON and sends angle query commands to all the sensory indication modules 104 in sequence to retrieve all the sensor angle readings. The microcontroller 506 then performs the posture check algorithm described in detail below. The outcome of this algorithm is to turn ON or OFF a feedback indicator 408. If a feedback indicator 408 must be turned ON, then the microcontroller 506 sends the ON command to the appropriate sensor and programs a short delay in the timer. If the posture is good and no activity of the feedback indicator 408 is required, then the microcontroller 506 programs a long delay in the timer. Once done with the posture check, the microcontroller 506 also sends posture data and status to an external device 602, if present and enabled. At this point the microcontroller 506 is done with the current processing and proceeds to enter sleep mode. While in sleep mode, an actuation of an interactive unit 204 (e.g., a push button pressed by the user) will also trigger the microcontroller 506 to power up and resume processing. A push button press is also detected while the CPU is ON.

When actuation of an interactive unit 204 is detected, the microcontroller 506 determines if a request to save the current posture as reference has been made (short duration button press) or the user wishes to turn OFF the device (long duration button press). If a save feature is requested, the microcontroller 506 saves the latest angle readings in non-volatile memory. Otherwise, the microcontroller 506 turns OFF all devices, including the internal clock and timer, stops all processing, and enters the OFF Mode. While in this very low power state however, specialized circuits inside the microcontroller 506 monitor the interactive unit 204 input. If an actuation of the interactive unit 204 is detected, the circuits trigger the microcontroller 506 to start its internal clock again and resume processing.

When powering up from the OFF Mode the microcontroller 506 determines if the reference posture needs to be set (based on the interactive unit 204). If so, the microcontroller 506 processes every timer timeout as described above and reads all the sensor angles but will not run the posture check algorithm. Instead, the microcontroller 506 commands the sensory indication modules 100 to run the feedback indicator 408 in a specific manner (e.g., each vibration motor vibrating in short bursts sequentially). This notifies the user in repetitive short bursts that the device is waiting to set the reference posture. The control module 104 remains in this mode until the actuation of the interactive unit 204 is detected for saving the setting, at which time microcontroller 506 saves the reference posture and switches to checking the posture. On power up, if microcontroller 506 detects actuation of the interactive unit 204 for as a recall function, microcontroller 506 retrieves the last saved reference posture from non-volatile memory and uses it as the reference posture as it immediately starts running the posture algorithm.

Figure 11C:
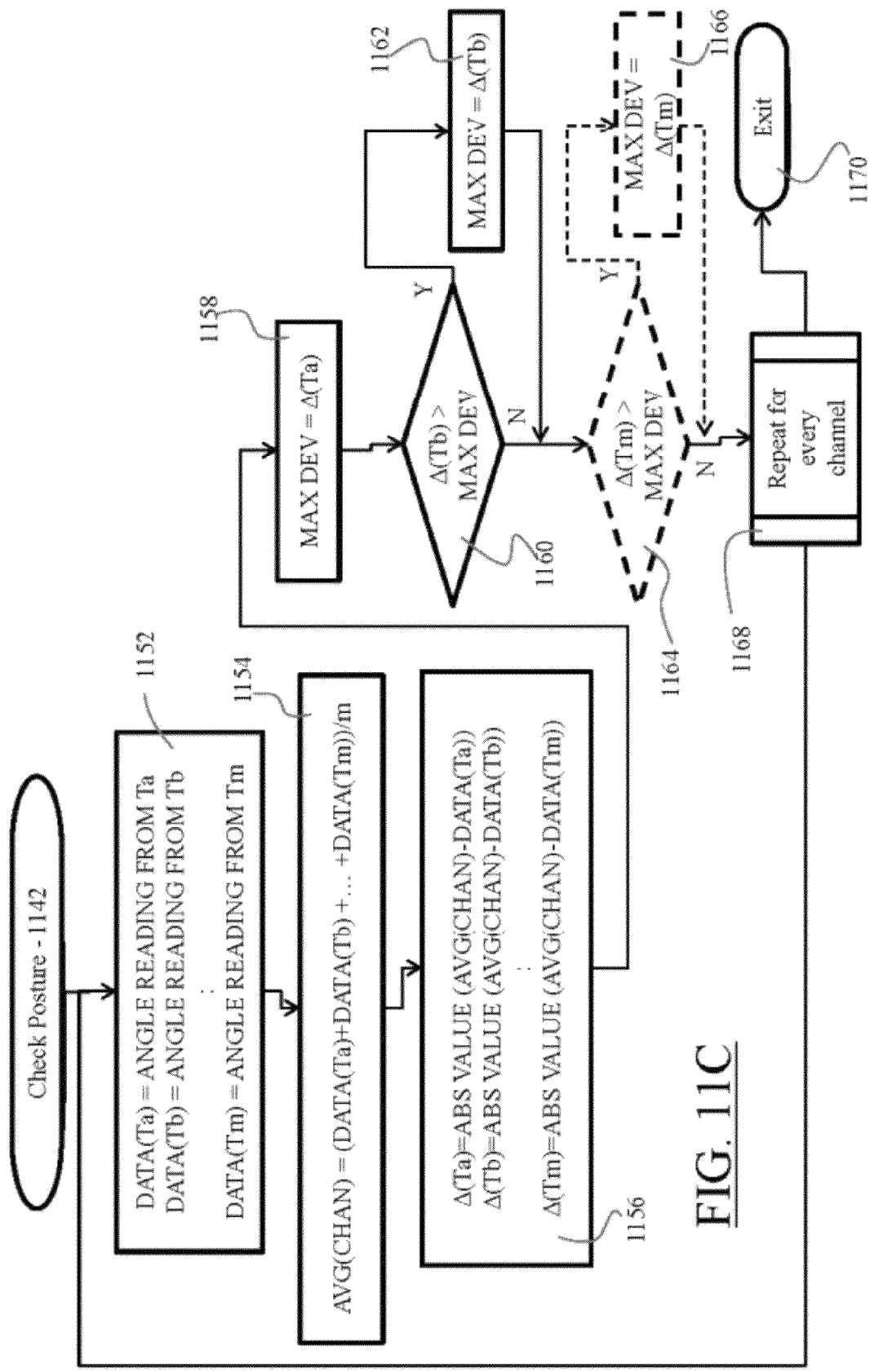

As illustrated in detail in FIGS. 11A to 11C, the microcontroller 506 is generally in a power save mode (at operational act 1102) for the first adaptive time period T1, with a duration of the first adaptive time period T1 varying depending on responses from external devices (such as the sensory indication modules 100). As illustrated, at the operational act 1104 the microcontroller 506 periodically determines if the first adaptive time period T1 has expired. If the microcontroller 506 determines that the first adaptive time period T1 has not expired, the microcontroller 506 at the operational acts 1106 and 1108 determines if the interactive unit 204 has been actuated for one of a first and second actuation durations, with the first actuation duration shorter than the second actuation duration.

It should be noted that the flow diagrams in FIGS. 11A and 11B illustrate the flow of the functionality of control module 104 that uses an interactive unit 204 comprised of a single push button actuator. Accordingly, the single push button actuator is implemented such that if it is pressed for various durations, for example, a first duration (operational act 1106), it may trigger one set of functions whereas if the same actuator is pressed for a second duration or some other third duration or in a sequence other functions may be triggered. Therefore, it should be apparent to those skills in the art that operational acts 1106, 1108, 1114, 1116, and 1134 associated with the actuation of the interactive unit 204 may easily be replaced and represented by other operational acts, depending on the type of interactive unit 204 used, without affecting the logical flow illustrated in FIGS. 11A to 11D. For example, instead of a single push button, a touch screen that may include a set of dedicated soft-button icons for specific functions may be used, such as a dedicated ON, OFF, and set reference soft-button icons. As a specific example, the microcontroller 506 may determine if a wakeup soft-button icon at operational act 1106 has been actuated or a second soft-button icon for deactivating a timer (at operational act 1108) has been pressed instead of the respective first and second duration pressing of a single push button, all without affecting the logical flow of the operations. Therefore, FIGS. 11A and 11B are only one exemplary implementation of the logical flow of operations that make use of an exemplary single push button as an example of the interactive unit 204, and should not be limiting. Accordingly, references to a single push button switch (and its duration of operations) throughout the remainder of the disclosure in relations to FIGS. 11A to 11D are meant as illustrative and for convenience of example, only.

As further illustrated in FIG. 11A, if microcontroller 506 determines that the interactive unit 204 as the exemplary single push button switch has not been actuated for one of the first (shorter) and second (longer) actuation durations and the first adaptive time period T1 is not expired, the microcontroller 506 maintain the power save mode (operational act 1102). If the microcontroller 506 determines that the interactive unit 204 has been actuated for second actuation duration (at operational act 1108) while the first adaptive time period T1 has not expired, the microcontroller deactivates the first adaptive time period T1 at the operational act 1110, and places the apparatus to OFF mode at operational act 1112. This is equivalent to a simple OFF switch that turns OFF a device. That is, if using another type of an interactive unit 204 that implements a dedicated OFF switch for the device of the present invention, the same logic flow can be used but instead of determining the second duration of actuation of the single button at the operational act 1108, the microcontroller 506 would determine if an OFF switch mechanism has been actuated (at operational act 1108). If the microcontroller determines at the operational act 1108 that the OFF switch has be actuated, the microcontroller 506 would deactivate the timer at operational act 1110, and turn OFF the device at operational act 1112, without any change in the logical flow of the operations of the microcontroller 506 illustrated in FIGS. 11A to 11D.

While the apparatus is OFF, if microcontroller 506 determines that the interactive unit 204 has not been actuated for one of the second and first actuation durations (operational acts 1114 and 1116), the microcontroller remains OFF. This is equivalent to not turning ON the device. Further, while the apparatus is OFF, if the interactive unit 204 has been actuated for second actuation duration, the microcontroller is activated, recalls saved users preferences, and activates the first adaptive time period T1 (at operational acts 1118 and 1120). On the other hand, if the interactive unit 204 has been actuated for first actuation duration (operational act 1116), the microcontroller 506 only activates the first adaptive time period T1 at the operational act 1120, and enters the power save mode 1102 via operational act 1122. Therefore, when turning ON the sensory indication modules 100, the user may actuate the interactive unit 204 (which may include a soft-button icon that is dedicated for a recall function) to recall the last saved reference posture (operational acts 1114, 1118, and 1120) or use the ON button icon to simply turn ON the device without the recall function (operational acts 1116 and 1120), all without affecting the logical flow of the control module 104.

As further illustrated in FIGS. 11A and 11B, if the microcontroller 506 determines that one of the first adaptive time period T1 has expired (at operational act 1104) and the interactive unit 204 has been actuated for the first actuation durations (operational act 1106), the microcontroller 506 forwards a first command (a wake up command) to sensory indication modules 100 at the operational act 1126. In addition, the microcontroller 506 also forwards a first query (in the form of angle measurements) to the modules 100, and receives a first response to the first query at the operational acts 1128 and 1130, respectively. Thereafter, at the operational act 1132 the microcontroller 506 determines if the first response has been received from all sensory indication modules 100. If the microcontroller 506 determines that the first response has been received from all the sensory indication modules 100, the microcontroller 506 at the operational act 1134 determines if the interactive unit 204 has been actuated for the first actuation durations. If not, the microcontroller 506 determines if a user preferred reference is set at the operational act 1136. If microcontroller 506 determines that user preferred reference is not set, the feedback indicator 408 is activated and the first adaptive time period T1 is modified for a longer duration, increasing the duration of the power save mode of the microcontroller at the operational acts 1138 and 1140, respectively.

If microcontroller 506 determines at the operational act 1136 that user preferred reference is set, the microcontroller 506 checks for posture by comparing the received responses with the user set preferred references by a predefined process 1142. If received responses are commensurate with user set preferred references at the operational act 1144 (e.g., good posture), the first adaptive time period T1 is modified for a longer duration, increasing the duration of the power save mode of the microcontroller 506 at the operational act 1140. Otherwise, the feedback indicator 408 is activated at the operational act 1138 and the first adaptive time period T1 is modified and set for a shorter duration at the operational act 1140. If microcontroller 506 determines that the interactive unit 204 has been actuated for the first actuation durations (operational act 1134), the microcontroller 506 sets received responses from the sensory indication modules 100 as user preferred reference (operational act 1150), and the set user preferences are communicated externally for display and analysis (at the operational acts 1146 and 1148, respectively).

FIG. 11C is an exemplary flow diagram for checking posture in accordance with the present invention. In other words, FIG. 11C illustrates describes the processing of the sensor angle data and logic used to determine if a feedback indicator such as a vibration motor needs to be turned ON to alert the user of a bad posture and more importantly, to avoid false alarms (e.g., due to the user bending to pickup and object or when user lying down). For this exemplary implementation, sensor angle data from several consecutive readings (e.g., three readings) are continuously saved as DATA(T−2), DATA (T−1), and DATA(T). The average of the readings is computed as AVE (CHAN), with CHAN being the channels for each X, Y, and Z axis. The maximum deviation from AVE (CHAN) is computed as MAX DEVIATION(CHAN). The average and max deviation results are compared with high and low limits for large angles and acceleration limit values. If the results exceed any of the limits, then no further posture check is performed and no feedback indicator 408 is allowed to turn ON.

A long timer delay (e.g., about 10 seconds) is setup before the algorithm is run again. If the results don't exceed the limits then the proper posture check is performed using the AVE(CHAN) data checked against the saved reference posture angle (+/−3 degrees). If a deviation is detected and depending on the direction of deviation and angle axis, the appropriate feedback indicator is commanded to turn ON in a specific manner (e.g., a vibration motor activates in short single or double burst, or single long burst). Thereafter, a short (about 1 second) timer delay is setup before the algorithm is run again. If no deviation is detected, a medium (about 3 seconds) timer delay is setup before the algorithm is run again. The microcontroller 506 feeds every angle sensor output through this algorithm. The X or forward-backward axis is run first starting at the top sensor at the T1 vertebra. Then, the Y or left-right axis is run again starting at the top sensor at the T1 vertebra, and then the Z. This sequence encourages the user to always correct his or her posture from the top down and in the forward-backward direction first.

Referring to the details of FIG. 11C, as was illustrated in FIG. 11B, the predefined process 1142 compares the received responses with user preferred references in accordance with the operational acts illustrated in FIG. 11C by obtaining a plurality of responses (angles read) in the form of Data($T_a$), Data($T_b$), . . . Data($T_m$) at different time intervals $T_a$, $T_b$, . . . $T_m$ from each of the sensory indication modules 100 at the operational act 1152. The angles are then averaged at the operational act 1154 by calculating an average AVG of the plurality of responses obtained at different time intervals as follows:

$$AVG(Channel) = (Data(T_a) + Data(T_b) + \ldots + Data(T_m))/m$$

Where m is an integer value for the number of time interval readings.

At the operational act 1156, the microcontroller 506 calculates simple deviations from the average of the plurality of responses obtained at different time intervals as follows:

$$\Delta(T_a) = ABS(AVG(Channel) - Data(T_a))$$
$$\Delta(T_b) = ABS(AVG(Channel) - Data(T_b))$$
$$\vdots$$
$$\Delta(T_m) = ABS(AVG(Channel) - Data(T_m)).$$

At operational acts 1158 to 1166 the microcontroller 506 determines the maximum deviation MAX DEV as follow:

$$MAX\ DEV(Channel) = MAX\ (\Delta(T_a), \Delta(T_b), \ldots \Delta(T_m)).$$

At operational act 1168 repeats the above for every channel (X, Y, and Z angle of every sensory indication module 100).

The microcontroller 506 then determines if the AVG(Channel) or the MAX DEV (Channel) are outside defined maximum parameters, and if so, the microcontroller 506 sets the first adaptive time period T1 duration and disable the indicators 408. This may occur when the user is actually and intentionally (consciously) performing acts that are outside the norm of an activity for which the posture training device is programmed. For example, user bends to pickup an item, making extreme moves that fall outside normal activity of walking (outside the AVG and MAX predefined parameters for the activities of walking or excessive motion). Accordingly, for example, the indicator 408 need not be activated to inform the user to correct posture when the user is consciously bending to pick up an item. Otherwise, microcontroller 506 determines if AVG(Channel) is outside the user set preferences. If the microcontroller 506 determines that AVG (Channel) is outside the user set preferences, microcontroller 506 determines which specific parameter within AVG(Channel) (the X, Y, Z angles) is outside user set preference, and generates a unique stimulation using the feedback indicator 408 specifically associated with that parameter, and sets the first adaptive time period duration T1 to a shorter duration. For example, the user may be leaning too much forward, which means that the feedback indicator 408 in the form of a vibration motor may be activated in two quick bursts informing user by the vibration stimulation of the two quick bursts of motor that the user needs to correct posture by leaning a bit back. As another example, if the user leans too much backward or to the right, the feedback indicator 408 may be activated in single or triple bursts, clearly informing and instructing user to appropriately correct posture. Any other stimulation to inform the user to appropriately correct posture may also be used, such as unique audio outputs for lateral deviation corrections of posture and so on. Otherwise, if the microcontroller 506 determines that AVG(Channel) is not outside the user set preferences, the microcontroller 506 sets the first adaptive time period duration T1 to an average duration.

Figure 11D:
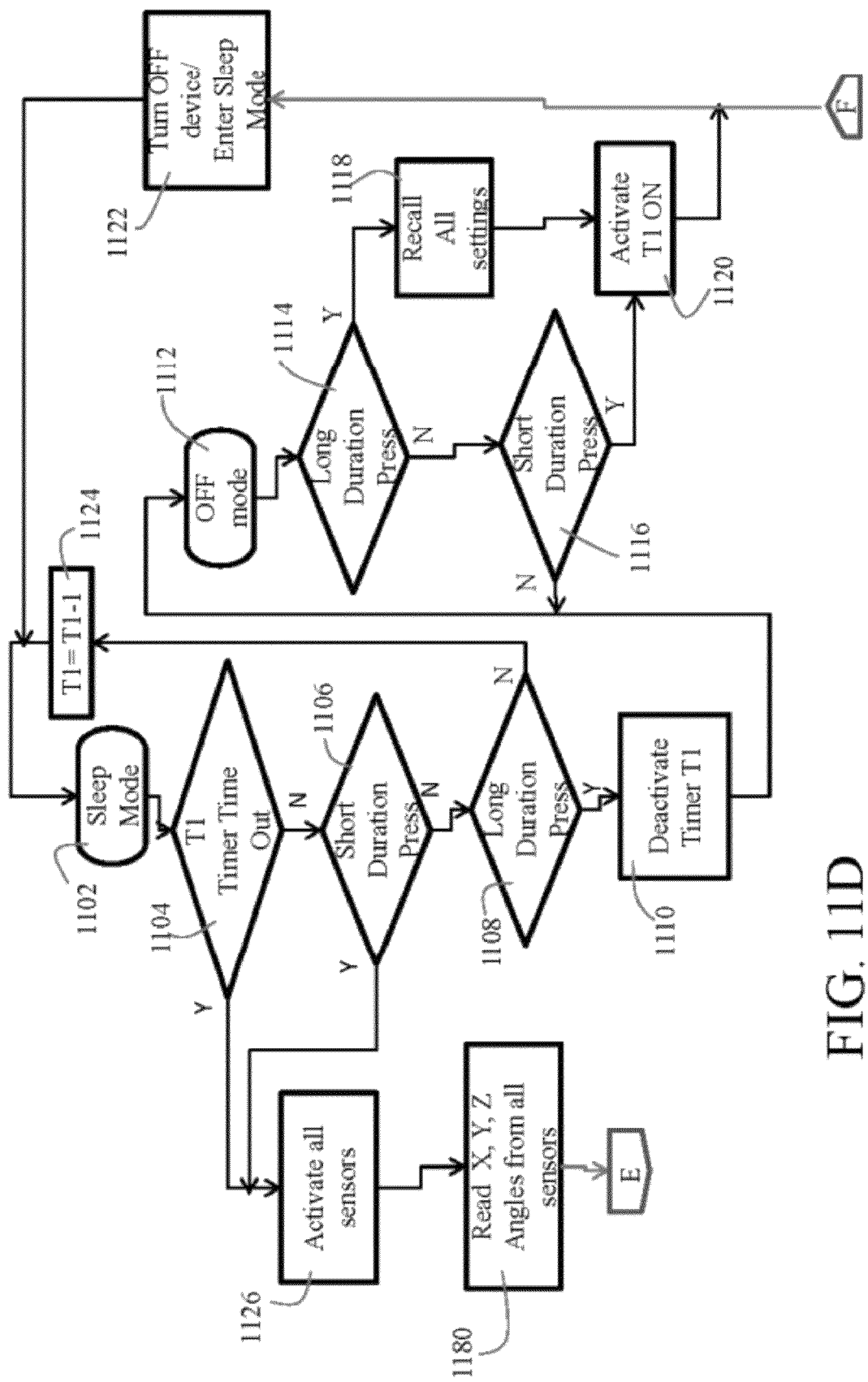

FIG. 11D is an exemplary partial schematic flow block diagram of the functionality of the control module 904 in accordance with the present invention. Only FIG. 11A of the control module 104 has been reproduced as FIG. 11D for the control module 904. The flow diagram of FIG. 11D includes similar corresponding or equivalent components, interconnections, and or cooperative relationships as the flow diagram in FIG. 11A to 11C described above. Therefore, for the sake of brevity, clarity, convenience, and to avoid duplication, the general description of FIG. 11D will not repeat every corresponding or equivalent component and or interconnections that has already been described above in relation to flows that are shown in FIGS. 11A to 11C.

In the alternate implementation where the sensory induction modules 100 only house an accelerometer sensor 404 and the feedback indicator 408, and the analog X, Y, and Z angle outputs are brought to a multiple input ADC inside the control module 104, the network line 414A is eliminated and the control module 104 directly controls the ADC and acquires the sensor angle values without having to send individual commands to the sensors, and similarly, the control module 104 directly controls the feedback indicators 408 without having to send the commands. The same posture check algorithm is used and in the same sequence.

As illustrated in detail FIG. 11D, the microcontroller 506 forwards a first command (wake up command) to external devices (e.g., the sensory indication modules 900), and simply receives data from external devices at operational act 1180. In other words, given the direct connections between the sensory indication modules 900 and the control module 904 (FIG. 9), the operational acts 1128 to 1132 loop illustrated in FIG. 11A is merely replaced by one read command 1180.

Although the invention has been described in considerable detail in language specific to structural features and or method acts, it is to be understood that the invention defined in the appended claims is not necessarily limited to the specific features or acts described. Rather, the specific features and acts are disclosed as preferred forms of implementing the claimed invention. Stated otherwise, it is to be understood that the phraseology and terminology employed herein, as well as the abstract, are for the purpose of description and should not be regarded as limiting. Therefore, while exemplary illustrative embodiments of the invention have been described, numerous variations and alternative embodiments will occur to those skilled in the art. For example, the sensory indication modules 100 may be directly coupled with a surface, without using the module support. For example, this can be a direct coupling of the sensory indication modules 100 with the skin of the user (using suction mechanism, removable adhesives, etc.). Such variations and alternate embodiments are contemplated, and can be made without departing from the spirit and scope of the invention.

It should further be noted that throughout the entire disclosure, the labels such as left, right, front, back, top, bottom, forward, reverse, clockwise, counter clockwise, up, down, or other similar terms such as upper, lower, aft, fore, vertical, horizontal, oblique, proximal, distal, parallel, perpendicular, transverse, longitudinal, etc. have been used for convenience purposes only and are not intended to imply any particular fixed direction or orientation. Instead, they are used to reflect relative locations and/or directions/orientations between various portions of an object.

In addition, reference to "first," "second," "third," and etc. members throughout the disclosure (and in particular, claims) is not used to show a serial or numerical limitation but instead is used to distinguish or identify the various members of the group.

In addition, any element in a claim that does not explicitly state "means for" performing a specified function, or "step for" performing a specific function, is not to be interpreted as a "means" or "step" clause as specified in 35 U.S.C. Section 112, Paragraph 6. In particular, the use of "step of," "act of," "operation of," or "operational act of" in the claims herein is not intended to invoke the provisions of 35 U.S.C. 112, Paragraph 6.

What is claimed is:

1. An apparatus, comprising:
sensory indication modules intimately associated with vertebra for detection of orientation and acceleration of vertebra, the sensory indication modules include:
an identification (ID) mechanism for identifying a sensory indication module that generates a unique analog ID signal;
a sensor for sensing the angle of the vertebra in relation to a true vertical and acceleration, and generating a first analog signal;
an Analog to Digital Converter (ADC) for digitizing the analog ID signal and the first analog signal for processing by a microprocessor;
a sensor actuation mechanism for periodically activating the sensor for detection;
a memory unit for storing data for use by the microprocessor;
a timer for synchronization of various functionalities of the sensory indication modules;
sensory indication module communication unit for communication of signals with the microprocessor and external devices;
a feedback indicators for communicating improper angular orientation of the vertebra with which the identified sensory indication module is associated.

2. The apparatus as set forth in claim 1, wherein:
the ID mechanism is an impedance that generates the unique analog ID signal that identifies the sensory indication module for unique association of the identified sensory indication module with a specific vertebra.

3. The apparatus as set forth in claim 1, wherein:
the sensor is a miniaturized multi-axis accelerometer.

4. The apparatus as set forth in claim 1, wherein:
the sensory indication module communication unit is asynchronous receiver transmitter.

5. The apparatus as set forth in claim 1, wherein:
the feedback indicator is a vibration motor that is actuated by a vibration actuator based on a command from the microprocessor.

6. An apparatus, comprising:
sensory indication modules that include a microprocessor;
the microprocessor periodically determines if there is a wake up command from a microcontroller of a control module;
if the microprocessor determines that there is no wake up command from the microcontroller of the control module, the microprocessor reverts back to sleep mode;
if the microprocessor determines that there is a wake up command from the microcontroller of the control module, the microprocessor is activated, which, in turn, activates a sensor for a first duration, and clears receiver buffer;
the microprocessor determines if there is a new command received from the microcontroller;
if the microprocessor determines that no new command is received from the microcontroller, the microprocessor reads angles of a vertebra through a sensor, saves the read angles, and determines if the first duration has expired;
if the microprocessor determines that the first duration has expired, the apparatus is entered into a low power sleep mode by the microcontroller of the control module;
if the microprocessor determines that the first duration has not expired, the receiver buffer is cleared, and the microprocessor determines if a new command is received from the microcontroller;
if the microprocessor determines that a new command is received from the microcontroller, the microprocessor checks the received command ID to determine if the received command from the microcontroller is intended for the sensor to which the received command is sent;
if the microprocessor determines that the command received from the microcontroller is intended for the sensor to which the command is sent, the microprocessor determines if the command received is an angle query command; otherwise, the receiver buffer is cleared;
if the microprocessor determines that command received is an angle query command, the microprocessor sends the saved sensed angular orientations to the microcontroller, and the receiver buffer is cleared;
if the microprocessor determines that command received is not the angle query command, the microprocessor determines if the command received is a command to activate an indicator;
if the microprocessor determines that command received is a command to activate the indicator, a second duration is set for activation of the indicator, the indicator is activated for the second duration, and the microcontroller enters the apparatus into a low power sleep mode;
if the microprocessor determines that command received is not a command to activate the indicator, the microprocessor determines if the command received is a reset command;
if the microprocessor determines that command received is a reset command, the microprocessor clears and resets all registers, and the microcontroller enters the apparatus into a low power sleep mode.

7. An apparatus, comprising:
a control module that includes a microcontroller, which is generally in a power save mode for a first adaptive time period, with a duration of the first adaptive time period varying depending on responses from external devices;
the microcontroller periodically determines if the first adaptive time period has expired;
if the microcontroller determines that the first adaptive time period has not expired, the microcontroller determines if an interactive unit has been actuated for one of a first and second actuation durations, with the first actuation duration shorter than the second actuation duration;
if microcontroller determines that the interactive unit has not been actuated for one of the first and second actuation durations, the microcontroller maintain the power save mode;
if the microcontroller determines that the interactive unit has been actuated for second actuation duration while the first adaptive time period has not expired, the microcontroller deactivates the first adaptive time period, and places the apparatus to OFF mode;
when the apparatus is OFF, if microcontroller determines that the interactive unit has not been actuated for one of the first and second actuation durations, the microcontroller remains OFF;
further, when the apparatus is OFF, if the interactive unit has been actuated for second actuation duration, the microcontroller is activated, recalls saved users preferences, and activates the first adaptive time period; if the interactive unit has been actuated for first actuation duration, the microcontroller only activates the first adaptive time period, and enters the power save mode;

if the microcontroller determines that one of the first adaptive time period has expired and the interactive unit has been actuated for the first actuation durations, the microcontroller forwards a first command to external devices;

the microcontroller further forwards a first query to the external devices, and receives a first response to the first query;

the microcontroller determines if the first response has been received from all external devices; if the microcontroller determines that the first response has been received from all external devices, the microcontroller determines if the interactive unit has been actuated for the first actuation durations;

if microcontroller determines that the interactive unit has not been actuated for the first actuation durations; the microcontroller determines if a user preferred reference is set;

if microcontroller determines that user preferred reference is not set; an indicator is activated and the first adaptive time period is modified for a longer duration, increasing the duration of the power save mode of the microcontroller;

if microcontroller determines that user preferred reference is set, the microcontroller compares received responses with user preferred references; if received responses are commensurate with user preferred references, the first adaptive time period is modified for a longer duration, increasing the duration of the power save mode of the microcontroller, otherwise, an indicator is activated and the first adaptive time period is modified for a shorter duration;

if microcontroller determines that the interactive unit has been actuated for the first actuation durations; the microcontroller sets received responses from external devices as user preferred reference.

8. The apparatus as set forth in claim 7, wherein:
set user preferences are communicated externally for display and analysis.

9. The apparatus as set forth in claim 8, wherein:
comparing the received responses with user preferred references includes:

obtaining a plurality of responses Data(Ta), Data(Tb), . . . Data(Tm) at different time intervals Ta, Tb, . . . Tm, with m an integer interval;

calculating an average AVG of the plurality of responses obtained at different time intervals:

$$AVG(Channel)=(Data(Ta)+Data(Ta)+\ldots+Data(Tm))/m;$$

calculating simple deviations from the average of the plurality of responses obtained at different time intervals;

$$\Delta(Ta)=ABS(AVG(Channel)-Data(Ta))$$

$$\Delta(Tb)=ABS(AVG(Channel)-Data(Tb))$$

$$\Delta(Tm)=ABS(AVG(Channel)-Data(Tm))$$

determining the maximum deviation MAX DEV;

$$MAX\ DEV(Channel)=MAX(\Delta(Ta),\Delta(Tb),\ldots\Delta(Tm));$$

repeat for every channel;

the microcontroller determines if the AVG(Channel) or the MAX DEV (Channel) are outside defined parameters, and if so, set the first adaptive time period duration and disable the feedback indicators;

otherwise, microcontroller determines if AVG(Channel) is outside the user set preferences; if the microcontroller determines that AVG(Channel) is outside the user set preferences, microcontroller determines which specific parameter within AVG(Channel) is outside user set preference, and generates a unique indicator specifically associated with that parameter, and sets the first adaptive time period duration to a shorter duration;

otherwise, set the first adaptive time period duration to an average duration.

* * * * *